United States Patent
Darwin et al.

(10) Patent No.: US 9,206,241 B2
(45) Date of Patent: Dec. 8, 2015

(54) MODIFIED PROKARYOTIC UBIQUITIN-LIKE PROTEIN AND METHODS OF USE THEREOF

(71) Applicants: Katerina Heran Darwin, New York, NY (US); Nicolaas Sebastiaan Merkx, Amsterdam (NL); Huib Ovaa, Amsterdam (NL)

(72) Inventors: Katerina Heran Darwin, New York, NY (US); Nicolaas Sebastiaan Merkx, Amsterdam (NL); Huib Ovaa, Amsterdam (NL)

(73) Assignee: New York University, New York, NY (US)

( * ) Notice: Subject to any disclaimer, the term of this patent is extended or adjusted under 35 U.S.C. 154(b) by 0 days.

(21) Appl. No.: 13/875,599

(22) Filed: May 2, 2013

(65) Prior Publication Data

US 2013/0295595 A1    Nov. 7, 2013

Related U.S. Application Data

(60) Provisional application No. 61/641,521, filed on May 2, 2012.

(51) Int. Cl.
 *C07K 14/35* (2006.01)
 *C12Q 1/18* (2006.01)

(52) U.S. Cl.
 CPC . *C07K 14/35* (2013.01); *C12Q 1/18* (2013.01); *G01N 2333/35* (2013.01)

(58) Field of Classification Search
 CPC .............. C07K 14/35; C07K 16/1289; C12N 2740/16022; C12Q 1/6837; G01N 2333/35
 See application file for complete search history.

(56) References Cited

U.S. PATENT DOCUMENTS

2010/0055715 A1    3/2010    Pearce et al.

OTHER PUBLICATIONS

Pearce et al., Ubiquitin-Like Protein Involved in the Proteasome Pathway of Mycobacterium tuberculosis., Science (Nov. 14, 2008), vol. 322, No. 5904, pp. 1104-1107.*
Rv2111c (last viewed on Aug. 27, 2014).*
FabD of Mycobacerium smegmatis (last viewed on Aug. 27, 2014).*
P9WIL7 (last viewed on Aug. 27, 2014).*
Burns et al., "Pupylation versus ubiquitylation: tagging for proteasome-dependent degradation", Cell Microbiol, 2010, 12:424-431.
Burns et al., "Depupylation of prokaryotic ubiquitin-like protein from mycobacterial proteasome substrates", Mol Cell, 2010, 39:821-827.
Burns et al., "Prokaryotic ubiquitin-like protein provides a two part degron to mycobacterium proteasome substrates", J Bact, 2010, 192:2933-2935.
Dang et al., "Kinetic and mechanistic studies on the hydrolysis of ubiquitin C-terminal 7-amido-4-methylcoumarin by deubiquitinating enzymes", Biochemistry, 1998, 37:1868-1879.

(Continued)

*Primary Examiner* — Alexander Kim
(74) *Attorney, Agent, or Firm* — Klauber & Jackson LLC

(57) ABSTRACT

Methods for making and using substrates of deamidase of prokaryotic ubiquitin-like protein (Dop) are described herein. More particularly, modified prokaryotic ubiquitin-like protein (Pup) and functional fragments thereof that serve as exemplary Dop substrates are described and encompassed herein. Screening methods to identify modulators of Dop and Pup activity and use of modulators identified thereby are also described. Methods of using modulators that are identified as inhibitors of Dop and Pup activity for treating diseases/conditions associated with *Mycobacterium tuberculosis* (Mtb) infection, such as tuberculosis and leprosy, are also envisioned.

14 Claims, 7 Drawing Sheets

(56) References Cited

OTHER PUBLICATIONS

El Oualid et al., "Chemical synthesis of ubiquitin, ubiquitin-based probes, and diubiquitin", Angew Chem Int Ed Engl, 2010, 49, 10149-10153.
Festa et al., "Prokaryotic ubiquitin-like protein (Pup) proteome of Mycobacterium tuberculosis", PLoS One, 2010, 5:1, e8589.
Imkamp et al., "Deletion of dop in Mycobacterium smegmatis abolishes pupylation of protein substrates in vivo", Mol Microbiol, 2010, 75:744-754.
Imkamp et al., "Dop functions as a dupupylase in the prokaryotic ubiquitin-like modification pathway", EMBO, 2010, 11:791-797.
Merkx et al., "Synthesis and evaluation of a selective fluorogenic pup derived assay reagent for dop, a potential drug target in mycobacterium tuberculosis", Chembiochem, 2012, 13:2056-2060.
Pearce et al., "Identification of substrates of the Mycobacterium tuberculosis proteasome", The EMBO J, 2006, 25:5423-5432.
Striebel et al., "Bacterial ubiquitin-like modifier Pup is deamidated and conjugated to substrates by distinct but homologous enzymes", Nat Struct Mol Biol, 2009, 16:647-651.
Striebel et al., "The mycobacterial Mpa-proteasome unfolds and degrades pupylated substrates by engaging Pup's N-terminus", EMBO J, 2010, 29:1262-1271.
Sutter et al., "A distinct structural region of the prokaryotic ubiquitin-like protein (Pup) is recognized by the N-terminal domain of the proteasomal ATPase Mpa", FEBS Letters, 2009, 583:3151-3157.
Sutter et al., "Prokaryotic ubiquitin-like protein (Pup) is coupled to substrates via the side chain of its C-terminal glutamate", Journal of Amer Chem Soc, 2010, 132:5610-5612.
Wang et al., "Binding-induced folding of prokaryotic ubiquitin-like protein on the Mycobacterium proteasomal ATPase targets substrates for degradation", Nat Struc Mol Biol, 2010, 17:1352-1357.
Borodovsky et al., "Chemistry-based functional proteomics reveals novel members of the deubiquitinating enzyme family", Chem Biol, 2002, 9:1149-1159.
Iyer et al. "Unraveling the biochemistry and provenance of pupylation: a prokaryotic analog of ubiquitination", Biology Direct, 2008, 3, 1-7.
Burns et al., "Mechanistic studies on the mycobacterial depupylase Dop", Enzymes, Coenzymes and Metabolic Pathways Meeting, Mexico, Nov. 17-21, 2011.
Cerda-Maira et al., "Molecular analysis of the prokaryotic ubiquitin-like protein (Pup) conjugation pathway in mycobacterium tuberculosis", Mol Microbiol, 2010, 77:1123-1135.

* cited by examiner

Fig. 5

Amino acid sequence of Pup (SEQ ID NO: 2):

MAQEQTKRGGGGGDDDDIAGSTAAGQERREKLTEETDDLLDEIDDVLEENAEDFVRAYVQKGGQ

Nucleic acid sequence of Pup (SEQ ID NO: 1):

M. tuberculosis H37Rv|Rv2111c|Rv2111c: 195 bp - CONSERVED
HYPO

Fig. 6

Dop nucleic acid sequence (SEQ ID NO: 3)

atgcagcggattatcggaacggaggtcgagtac
ggcatttcctcgccgtcggacccgaccgccaacccgatcctcacctcgacgcaggcggtg
ctggcatacgccgccgccgcggcattcagcgtgccaaacgcacccgttgggactacgag
gtggaatcgccgctgcgcgacgccgggcttcgatttgagtcgctcggccgggccgccg
ccggtggtcgacgccgacgaggtcggcgcggccaacatgatcctgaccaacggggcgcgg
ctgtatgtcgaccacgcgcaccggaatactccgcgcccgaatgcaccgacccgctggac
gcagtgatctgggacaaggcgggcgaacgcgtgatggaggccgctgcccgccatgtcgcc
agcgtgcccggggccgcgaaactgcagctgtacaagaacaacgtcgacggcaagggagcc
tcctacggtcgcacgagaactacctgatgtcgcggcagacaccgttctcggcgatcatc
accgggctgacccccttctggtatcccggcaggtggtgaccggctcgggccgggtcggc
atcgggccctcgggtgatgagcccggcttccagctatcccagcgttcggactacatcgag
gtcgaggtagggctggaaacaacgctcaagcgcggcatcatcaacacccgcgacgaaccg
cacgccgacgccgacaggtaccgccggctgcacgtcatcatcggcgacgccaaccttgcc
gagacgtcgacctatctgaagttgggtaccacggcgctggtgctcgacctgatcgaagaa
ggaccagcccacgcaatagatctgaccgacctggcgctggcccgccggtacatgcggtg
cacgcaatctcccgcgatccgtcgctgcgagcgaccgttgcgctggccgacggccgggaa
ctgaccggtcttgcgctgcaacggatctacctggaccgagtggctaagttggtggatagc
cgcgacccggacccgcgggcggccgacatcgtggaaacctgggcacacgtgctggatcag
ctcgagcgtgacccgatggattgcgcggagctgctggactggccggccaaactgcggctg
ctcgacggttttccggcagcgggagaacctgagctggtcggcgccccggctgcacctcgtc
gacctgcagtactccgatgtccggctggacaagggcctgtacaaccggctggtcgcgcgc
ggctcgatgaagcgtttagtcaccgaacaccaggtgctgagtgcggtggagaacccgccg
accgacacccgcgcgtatttccgcggcgaatgcctgcgccggttcggggctgatatcgcc
gcggctagctgggactcggtgatcttcgacctgggcggcgactcgctggttcgcatcccg
acgctggagccgttgcggggtagtaaggcgcatgttggtgcgttgctggattcggtggac
agtgccgtggagctggtagagcaactgaccgctgagcctcgctaa Dop amino acid sequence (SEQ ID NO: 4)
MQRIIGTEVEYGISSPSDPTANPILTSTQAVLAYAAAAGIQRAKRTRWDYEVESPLRDAR
GFDLSRSAGPPVVDADEVGAANMILTNGARLYVDHAHPEYSAPECTDPLDAVIWDKAGE
RVMEAAARHVASVPGAAKLQLYKNNVDGKGASYGSHENYLMSRQTPFSAIITGLTPFLVS
RQVVTGSGRVGIGPSGDEPGFQLSQRSDYIEVEVGLETTLKRGIINTRDEPHADADRYRR
LHVIIGDANLAETSTYLKLGTTALVLDLIEEGPAHAIDLTDLALARPVHAVHAISRDPSL
RATVALADGRELTGLALQRIYLDRVAKLVDSRDPDPRAADIVETWAHVLDQLERDPMDCA
ELLDWPAKLRLLDGFRQRENLSWSAPRLHLVDLQYSDVRLDKGLYNRLVARGSMKRLVTE
HQVLSAVENPPTDTRAYFRGECLRRFGADIAAASWDSVIFDLGGDSLVRIPTLEPLRGSK
AHVGALLDSVDSAVELVEQLTAEPR

```
                             SEQUENCE LISTING

<160> NUMBER OF SEQ ID NOS: 7

<210> SEQ ID NO 1
<211> LENGTH: 195
<212> TYPE: DNA
<213> ORGANISM: Mycobacterium tuberculosis

<400> SEQUENCE: 1
atggcgcaag agcagaccaa gcgtggcggt ggcggcggcg atgatgacga catcgccggc      60
agcaccgccg cgggccagga gcgtcgcgaa aagctgaccg aggagaccga cgatctgctc     120
gacgaaatcg acgacgtcct cgaggagaac gccgaggact cgtccgcgc atacgtccaa      180 aagggcggac agtga                                                      195

<210> SEQ ID NO 2
<211> LENGTH: 64
<212> TYPE: PRT
<213> ORGANISM: Mycobacterium tuberculosis

<400> SEQUENCE: 2

Met Ala Gln Glu Gln Thr Lys Arg Gly Gly Gly Gly Asp Asp Asp
 1               5                  10                  15

Asp Ile Ala Gly Ser Thr Ala Ala Gly Gln Glu Arg Arg Glu Lys Leu
             20                  25                  30

Thr Glu Glu Thr Asp Asp Leu Leu Asp Glu Ile Asp Asp Val Leu Glu
         35                  40                  45

Glu Asn Ala Glu Asp Phe Val Arg Ala Tyr Val Gln Lys Gly Gly Gln
     50                  55                  60

<210> SEQ ID NO 3
<211> LENGTH: 1518
<212> TYPE: DNA
<213> ORGANISM: Mycobacterium tuberculosis

<400> SEQUENCE: 3
atgcagcgga ttatcggaac ggaggtcgag tacggcattt cctcgccgtc ggacccgacc      60
gccaacccga tcctcacctc gacgcaggcg gtgctggcat acgccgccgc cgccggcatt     120
cagcgtgcca aacgcacccg ttgggactac gaggtggaat cgccgctgcg cgacgcccgg     180
ggcttcgatt tgagtcgctc ggccgggccg ccgccggtgg tcgacgccga cgaggtcggc     240
gcggccaaca tgatcctgac caacggggcg cggctgtatg tcgaccacgc gcacccggaa     300
tactccgcgc ccgaatgcac cgacccgctg gacgcagtga tctgggacaa ggcgggcgaa     360
cgcgtgatgg aggccgctgc ccgccatgtc gccagcgtgc ccggggccgc gaaactgcag     420
ctgtacaaga acaacgtcga cggcaaggga gcctcctacg ggtcgcacga gaactacctg     480
atgtcgcggc agacaccgtt ctcggcgatc atcaccgggc tgacccccctt tctggtatcc     540 cggcaggtgg tgaccggctc gggccgggtc ggcatcgggc cctcgggtga tgagcccggc     600
ttccagctat cccagcgttc ggactacatc gaggtcgagg tagggctgga acaacgctc      660
```

```
aagcgcggca tcatcaacac ccgcgacgaa ccgcacgccg acgccgacag gtaccgccgg    720
ctgcacgtca tcatcggcga cgccaacctt gccgagacgt cgacctatct gaagttgggt    780
accacggcgc tggtgctcga cctgatcgaa gaaggaccag cccacgcaat agatctgacc    840
gacctggcgc tggcccgccc ggtacatgcg gtgcacgcaa tctcccgcga tccgtcgctg    900
cgagcgaccg ttgcgctggc cgacggccgg gaactgaccg tcttgcgct gcaacggatc     960 tacctggacc gagtggctaa gttggtggat agccgcgacc cggacccgcg gcggccgac    1020 atcgtggaaa cctgggcaca cgtgctggat cagctcgagc gtgacccgat ggattgcgcg   1080
gagctgctgg actggccggc caaactgcgg ctgctcgacg gtttccggca gcgggagaac   1140
ctgagctggt cggcgccccg gctgcacctc gtcgacctgc agtactccga tgtccggctg   1200
gacaagggcc tgtacaaccg gctggtcgcg cgcggctcga tgaagcgttt agtcaccgaa   1260
caccaggtgc tgagtgcggt ggagaacccg ccgaccgaca cccgcgcgta tttccgcggc   1320
gaatgcctgc gccggttcgg ggctgatatc gccgcggcta gctgggactc ggtgatcttc   1380
gacctgggcg gcgactcgct ggttcgcatc ccgacgctgg agccgttgcg gggtagtaag   1440
gcgcatgttg gtgcgttgct ggattcggtg gacagtgccg tggagctggt agagcaactg   1500
accgctgagc ctcgctaa                                                 1518
```

<210> SEQ ID NO 4
<211> LENGTH: 505
<212> TYPE: PRT
<213> ORGANISM: Mycobacterium tuberculosis

<400> SEQUENCE: 4

```
Met Gln Arg Ile Ile Gly Thr Glu Val Glu Tyr Gly Ile Ser Ser Pro
 1               5                  10                  15

Ser Asp Pro Thr Ala Asn Pro Ile Leu Thr Ser Thr Gln Ala Val Leu
            20                  25                  30

Ala Tyr Ala Ala Ala Ala Gly Ile Gln Arg Ala Lys Arg Thr Arg Trp
        35                  40                  45

Asp Tyr Glu Val Glu Ser Pro Leu Arg Asp Ala Arg Gly Phe Asp Leu
    50                  55                  60

Ser Arg Ser Ala Gly Pro Pro Val Val Asp Ala Asp Glu Val Gly
65                  70                  75                  80

Ala Ala Asn Met Ile Leu Thr Asn Gly Ala Arg Leu Tyr Val Asp His
                85                  90                  95

Ala His Pro Glu Tyr Ser Ala Pro Glu Cys Thr Asp Pro Leu Asp Ala
           100                 105                 110

Val Ile Trp Asp Lys Ala Gly Glu Arg Val Met Glu Ala Ala Ala Arg
       115                 120                 125

His Val Ala Ser Val Pro Gly Ala Ala Lys Leu Gln Leu Tyr Lys Asn
   130                 135                 140

Asn Val Asp Gly Lys Gly Ala Ser Tyr Gly Ser His Glu Asn Tyr Leu
145                 150                 155                 160

Met Ser Arg Gln Thr Pro Phe Ser Ala Ile Ile Thr Gly Leu Thr Pro
                165                 170                 175

Phe Leu Val Ser Arg Gln Val Val Thr Gly Ser Gly Arg Val Gly Ile
           180                 185                 190

Gly Pro Ser Gly Asp Glu Pro Gly Phe Gln Leu Ser Gln Arg Ser Asp
       195                 200                 205

Tyr Ile Glu Val Glu Val Gly Leu Glu Thr Thr Leu Lys Arg Gly Ile
```

```
                    210                 215                 220

Ile Asn Thr Arg Asp Glu Pro His Ala Asp Ala Asp Arg Tyr Arg Arg
225                 230                 235                 240

Leu His Val Ile Ile Gly Asp Ala Asn Leu Ala Glu Thr Ser Thr Tyr
                    245                 250                 255

Leu Lys Leu Gly Thr Thr Ala Leu Val Leu Asp Leu Ile Glu Glu Gly
                260                 265                 270

Pro Ala His Ala Ile Asp Leu Thr Asp Leu Ala Leu Ala Arg Pro Val
            275                 280                 285

His Ala Val His Ala Ile Ser Arg Asp Pro Ser Leu Arg Ala Thr Val
290                 295                 300

Ala Leu Ala Asp Gly Arg Glu Leu Thr Gly Leu Ala Leu Gln Arg Ile
305                 310                 315                 320

Tyr Leu Asp Arg Val Ala Lys Leu Val Asp Ser Arg Asp Pro Asp Pro
                    325                 330                 335

Arg Ala Ala Asp Ile Val Glu Thr Trp Ala His Val Leu Asp Gln Leu
                340                 345                 350

Glu Arg Asp Pro Met Asp Cys Ala Glu Leu Leu Asp Trp Pro Ala Lys
            355                 360                 365

Leu Arg Leu Leu Asp Gly Phe Arg Gln Arg Glu Asn Leu Ser Trp Ser
370                 375                 380

Ala Pro Arg Leu His Leu Val Asp Leu Gln Tyr Ser Asp Val Arg Leu
385                 390                 395                 400

Asp Lys Gly Leu Tyr Asn Arg Leu Val Ala Arg Gly Ser Met Lys Arg
                    405                 410                 415

Leu Val Thr Glu His Gln Val Leu Ser Ala Val Glu Asn Pro Pro Thr
                420                 425                 430

Asp Thr Arg Ala Tyr Phe Arg Gly Glu Cys Leu Arg Arg Phe Gly Ala
            435                 440                 445

Asp Ile Ala Ala Ala Ser Trp Asp Ser Val Ile Phe Asp Leu Gly Gly
450                 455                 460

Asp Ser Leu Val Arg Ile Pro Thr Leu Glu Pro Leu Arg Gly Ser Lys
465                 470                 475                 480

Ala His Val Gly Ala Leu Leu Asp Ser Val Asp Ser Ala Val Glu Leu
                    485                 490                 495

Val Glu Gln Leu Thr Ala Glu Pro Arg
                500                 505

<210> SEQ ID NO 5
<211> LENGTH: 64
<212> TYPE: PRT
<213> ORGANISM: Mycobacterium tuberculosis
<220> FEATURE:
<221> NAME/KEY: misc_feature
<222> LOCATION: (64)...(64)
<223> OTHER INFORMATION: Xaa is a modified glutamic acid wherein a
      fluorescent moiety is attached via a side chain

<400> SEQUENCE: 5

Met Ala Gln Glu Gln Thr Lys Arg Gly Gly Gly Gly Asp Asp Asp
 1               5                  10                  15

Asp Ile Ala Gly Ser Thr Ala Gly Gln Glu Arg Arg Glu Lys Leu
                20                  25                  30

Thr Glu Glu Thr Asp Asp Leu Leu Asp Glu Ile Asp Asp Val Leu Glu
                35                  40                  45

Glu Asn Ala Glu Asp Phe Val Arg Ala Tyr Val Gln Lys Gly Gly Xaa
```

```
                  50                  55                  60

<210> SEQ ID NO 6
<211> LENGTH: 31
<212> TYPE: PRT
<213> ORGANISM: Mycobacterium tuberculosis
<220> FEATURE:
<221> NAME/KEY: misc_feature
<222> LOCATION: (31)...(31)
<223> OTHER INFORMATION: Xaa is a modified glutamic acid wherein a
      fluorescent moiety is attached via a side chain

<400> SEQUENCE: 6

Glu Glu Thr Asp Asp Leu Leu Asp Glu Ile Asp Asp Val Leu Glu Glu
 1               5                  10                  15

Asn Ala Glu Asp Phe Val Arg Ala Tyr Val Gln Lys Gly Gly Xaa
            20                  25                  30

<210> SEQ ID NO 7
<211> LENGTH: 21
<212> TYPE: PRT
<213> ORGANISM: Mycobacterium tuberculosis
<220> FEATURE:
<221> NAME/KEY: misc_feature
<222> LOCATION: (21)...(21)
<223> OTHER INFORMATION: Xaa is a modified glutamic acid wherein a
      fluorescent moiety is attached via a side chain

<400> SEQUENCE: 7

Asp Asp Val Leu Glu Glu Asn Ala Glu Asp Phe Val Arg Ala Tyr Val
 1               5                  10                  15

Gln Lys Gly Gly Xaa
            20
```

MODIFIED PROKARYOTIC UBIQUITIN-LIKE PROTEIN AND METHODS OF USE THEREOF

CROSS REFERENCE TO RELATED APPLICATIONS

This application claims priority under 35 USC §119(e) from U.S. Provisional Application Ser. No. 61/641,521, filed May 2, 2012, which application is herein specifically incorporated by reference in its entirety.

The research leading to the present invention was funded in part by NIH Grant No. AI0880875. The United States government has certain rights in the invention.

FIELD OF THE INVENTION

The present invention pertains to the fields of molecular biology, regulated protein degradation, and diagnostic and therapeutic medicine. More specifically, the invention relates to screening methods to identify modulators of prokaryotic ubiquitin-like protein (Pup) activity and use of modulators identified thereby for treating diseases/conditions associated with *Mycobacterium tuberculosis* (Mtb) or *Mycobacterium leprae* infection, such as tuberculosis and leprosy, respectively. Methods of making and using modified Pup proteins and fragments thereof are also encompassed herein.

BACKGROUND OF THE INVENTION

Several publications and patent documents are referenced in this application in order to more fully describe the state of the art to which this invention pertains. The disclosure of each of these publications and documents is incorporated by reference herein.

*Mycobacterium tuberculosis* (Mtb) is one of the world's deadliest pathogens, claiming about 1.5 million lives annually (Dye et al., *Lancet Infect Dis* 8, 233 (April, 2008). The occurrence of approximately 9 million new cases of Mtb a year and the increased emergence of antibiotic resistant strains necessitates the development of new anti-mycobacterial drugs. The Mtb proteasome and proposed cofactors, *Mycobacterium* proteasomal ATPase (Mpa) and proteasome accessory factor A (PafA), are essential for the pathogenicity of Mtb (Darwin et al., *Science* 302, 1963 (2003); Darwin et al, *Mol Microbiol* 55, 561 (2005); Gandotra et al, *Nat Med* 13, 1515 (December, 2007)), qualifying components of the Mtb proteasome system as potential drug targets.

Similar to the eukaryotic 20S proteasome, the Mtb proteasome is a multi-subunit barrel-shaped protease composed of two rings of catalytic β-subunits sandwiched by rings of α-subunits (Benaroudj et al, *Mol Cell* 11, 69 (January, 2003); Groll et al., *Nature* 386, 463 (Apr. 3, 1997); Hu et al., *Mol. Microbiol.* 59, 1417 (2006); Lin et al., *Mol. Microbiol.* 59, 1405 (2006); Unno et al., *Structure* 10, 609 (May, 2002)). The eukaryotic 26S proteasome is composed of a 20S core particle and one or two 19S regulatory caps, which include ATPases that recognize, unfold, and translocate substrates into the core for degradation [reviewed in Baumeister et al., *Cell* 92, 367 (1998)]. In Mtb, Mpa shares homology with regulatory cap ATPases that translocate proteins into the core. The present inventors previously identified substrates of the Mtb proteasome (Pearce et al., *EMBO J.* 25, 5423 (2006)), however, the mechanism(s) whereby these substrates were targeted for degradation was not elucidated. Proteins delivered to the eukaryotic proteasome are usually conjugated with ubiquitin, which covalently attaches to substrate lysines (Lys) as well as onto ubiquitin itself [reviewed in Hershko et al, *Annu Rev Biochem* 67, 425 (1998)]. Ubiquitin-like genes have not been identified in the Mtb genome, suggesting that substrate targeting to the Mtb proteasome occurs via an ubiquitin-independent mechanism.

The special properties of the Mtb cell wall combined with its extremely slow dividing time make efficient treatment of tuberculosis (TB) difficult. Current therapies make use of a combination of antibiotics that have to be taken daily for multiple months. The treatment has significant toxicity and is often accompanied with severe side effects. Moreover, multidrug-resistant strains of Mtb have developed. Therefore, the need for new TB drugs that inhibit targets that are different from those of currently used drugs is urgent. To minimize side effects, these new targets should ideally only be present in the disease causing bacteria and not in the human host.

SUMMARY OF INVENTION

A modified Pup comprising or consisting of amino acids spanning positions 1-63 of Pup (SEQ ID NO: 2), wherein the carboxylate of glycine at amino acid position 63 (Gly63) of SEQ ID NO: 2 is attached via a covalent linkage to a modified glutamic acid (Glu), wherein the modification is attached via a side chain of Glu. In an embodiment thereof, the modification is a fluorescent moiety. Compositions of each of which are also encompassed herein.

Also described herein is a modified Pup comprising or consisting of amino acids spanning positions 33-63 of Pup (SEQ ID NO: 2), wherein the carboxylate of glycine at amino acid position 63 (Gly63) of SEQ ID NO: 2 is attached via a covalent linkage to a modified glutamic acid (Glu), wherein the modification is attached via a side chain of Glu. In an embodiment thereof, the modification is a fluorescent moiety. Compositions of each of which are also encompassed herein.

In an embodiment described herein, the above modified Pups are attached to the fluorescent moiety via the gamma-carboxylate side chain of glutamic acid (Glu). As described herein, the residue added to the carboxylate of glycine at amino acid position 63 (Gly63) is a modified Glu wherein the modification (e.g., a fluorescent moiety) is on the gamma-carboxylate side chain of Glu. In a particular embodiment, the fluorescent moiety is AMC or TAMRA.

A method of making a modified Pup or functional fragment thereof comprising a C-terminus modification, wherein the C-terminus modification is a fluorescent moiety is also presented herein, the method comprising: a) providing amino acids 1-63 of Pup (SEQ ID NO: 2) or a fragment thereof comprising amino acids 33-63 of Pup, wherein the amino acids 1-63 of Pup (SEQ ID NO: 2) or the fragment thereof comprise a free C-terminal carboxylate; and b) coupling the amino acids 1-63 of Pup (SEQ ID NO: 2) or the fragment thereof comprising a free C-terminal carboxylate to H-(Glu (fluorescent moiety)-OH in the presence of condensing reagents to generate the modified Pup or functional fragment thereof comprising the C-terminus fluorescent moiety. In a particular aspect, the C-terminus fluorescent moiety is covalently attached to a side chain of the Glu residue. In a more particular aspect, the side chain is the gamma-carboxylate side chain of Glu. In another aspect, the fluorescent moiety is amino methyl coumarin (AMC) and the H-Glu (fluorescent moiety)-OH is H-Glu(AMC)-OH. The method may be performed using PyBOP and DIPEA as the condensing reagents.

In a further aspect of the method, the amino acids 1-63 of Pup (SEQ ID NO: 2) or a fragment thereof comprising amino acids 33-63 of Pup are generated using Fmoc-based linear solid-phase peptide synthesis (SPPS) or intein-based chemistry.

Also encompassed herein is a modified Pup comprising or consisting of amino acids spanning positions 1-64 of Pup (SEQ ID NO: 2), wherein a side chain of glutamic acid (Glu) at position 64 of SEQ ID NO: 2 is connected to the epsilon amine atom of a lysine (Lys) residue and the Lys residue is linked via its alpha amino atom to a fluorescent moiety. Compositions of each of which are also encompassed herein.

A method of making a modified Pup comprising a C-terminus modification, wherein the C-terminus modification is a fluorescent moiety is also presented herein, the method comprising: a) providing amino acids 1-64 of Pup (SEQ ID NO: 2) comprising a free C-terminal carboxylate; and b) coupling the amino acids 1-64 of Pup (SEQ ID NO: 2) in protected form and comprising a free C-terminal carboxylate to H-Glu(Lys (fluorescent moiety)—OH)—OH in the presence of a condensing reagent to generate the modified Pup comprising the C-terminal fluorescent moiety in which glutamic acid (Glu) is connected through its side chain to the epsilon amine atom of a lysine (Lys) residue, wherein the Lys residue is linked via its alpha amino atom to the fluorescent moiety. In a particular embodiment thereof, the coupling is performed after deprotection using trifluoroacetic acid 95%/water/2.5% and triisopropylsilane. An exemplary fluorescent moiety for use in this method is 5-tetramethylrhodamine (TAMRA) and the H-Glu(Lys(fluorescent moiety)—OH)—OH is H-Glu(Lys-TAMRA)-OH.

Also envisioned herein is a method for identifying a modulator of prokaryotic ubiquitin like protein (Pup) activity, comprising: contacting Pup or a functional fragment thereof with a test compound in the presence of deamidase of Pup (Dop), wherein the Pup or the functional fragment thereof comprises a C-terminus modification that confers a detectable signal that changes when linkage of the Pup or the functional fragment thereof to the C-terminus modification is severed; and measuring the detectable signal in the presence and absence of the test compound, wherein a change in detectable signal in the presence of the test compound relative to that detected in the absence of the test compound identifies the test compound as a modulator of Pup activity. In a particular embodiment thereof, the C-terminus modification is a fluorescent moiety. Suitable fluorescent moieties include amino methyl coumarin (AMC) or 5-tetramethylrhodamine (TAMRA). Exemplary Pup or functional fragments thereof comprising a C-terminus modification suited for use in this method are presented herein and others can be envisioned based on these molecules.

The method for identifying a modulator of Pup activity may be performed using cell lysates or in a suitable vessel using isolated, purified components in a Dop activity compatible buffer. Suitable cell lysates include those isolated from bacterial cells that either express endogenous Dop or are engineered to express Dop from an expression construct. Whether performed using cell lysates or isolated, purified components, the method may be performed using Dop that comprises a tag moiety (e.g., a histidine tag or the like that would facilitate isolation of Dop). In a particular embodiment, a change in detectable signal in the presence of the test compound relative to that detected in the absence of the test compound, as reflected in an increase in fluorescence, identified the test compound as an inhibitor of Pup activity.

In a further aspect, a method for identifying an inhibitor of deamidase activity of Dop is presented herein, the method comprising measuring the deamidase activity of Dop in the presence and absence of a test compound, wherein a decrease in deamidase activity in the presence of the test compound identifies the test compound as an inhibitor of Dop. In an embodiment thereof, the deamidase activity is assessed by determining fluorescent emissions of a fluorescent substrate, wherein the fluorescent substrate is Pup or a functional fragment thereof comprising a fluorescent moiety attached at the C-terminus. In a more particular embodiment, the fluorescent moiety is amino methyl coumarin (AMC) or 5-tetramethylrhodamine (TAMRA). Exemplary Pup or functional fragments thereof comprising a C-terminus modification suited for use in this method are presented herein and others can be envisioned based on these molecules.

The method for identifying an inhibitor deamidase activity of Dop may be performed using cell lysates or in a suitable vessel using isolated, purified components in a Dop activity compatible buffer. Suitable cell lysates include those isolated from bacterial cells that either express endogenous Dop or are engineered to express Dop from an expression construct. Whether performed using cell lysates or isolated, purified components, the method may be performed using Dop that comprises a tag moiety (e.g., a histidine tag or the like that would facilitate isolation of Dop).

Screening methods described herein may be adapted for high throughput screening.

In a further aspect, a method for identifying a compound as useful for the treatment of tuberculosis (TB) is described herein, the method comprising measuring deamidase activity of Dop in the presence or absence of a test agent; and determining whether the deamidase activity of Dop is decreased in the presence of the test agent, wherein if the activity is decreased in the presence of the test agent, the test agent is identified as a compound useful for the treatment of TB.

In yet a further aspect, a method for identifying a compound as useful for the treatment of leprosy is described herein, the method comprising measuring deamidase activity of Dop in the presence or absence of a test agent; and determining whether the deamidase activity of Dop is decreased in the presence of the test agent, wherein if the activity is decreased in the presence of the test agent, the test agent is identified as a compound useful for the treatment of leprosy.

Also encompassed herein are inhibitors of Pup activity and inhibitors of deamidase activity of Dop identified using methods described herein.

Other features and advantages of the invention will be apparent from the following description of the preferred embodiments thereof, and from the claims.

by treatment with Dop or the ATP-binding defective mutant DopE10A. B) Dop kinetics obtained with Pup(1-63)-Glu (AMC) (1a), inset: ESMS analysis of the cleavage reaction before (blue) and after (red) treatment with Dop. C) Dop kinetics obtained with Pup(33-63)-Glu(AMC) (1b), inset: analysis of the cleavage reaction before (blue) and after (red) treatment with Dop. RFU=relative fluorescence units.

Figure 4:
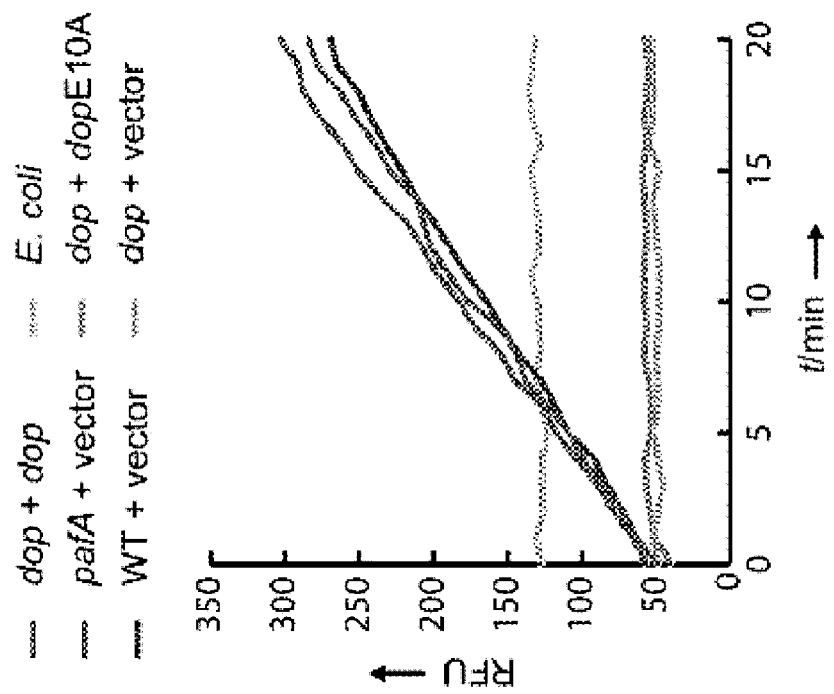

FIG. 4 shows hydrolytic activity in lysates of various Mtb and *E. coli* strains using Pup(1-63)-Glu(AMC) (1a) as the substrate. Lysates of pafA (green) and dop (grey, red, blue) mutants containing empty plasmid vector or vector with indicated genes were analyzed along with lysates from WT Mtb (purple) with empty vector and lysates of *E. coli* (orange) for hydrolysis of Pup(1-63)-Glu(AMC) (1a). RFU=relative fluorescence units.

FIG. 5 shows an amino acid sequence of Pup (SEQ ID NO: 2) encoded by SEQ ID NO: 1.

FIG. 6 shows an amino acid sequence of Dop (SEQ ID NO: 4) encoded by SEQ ID NO: 3. The corresponding NCBI accession number is ADJ67804.

Figure 7:
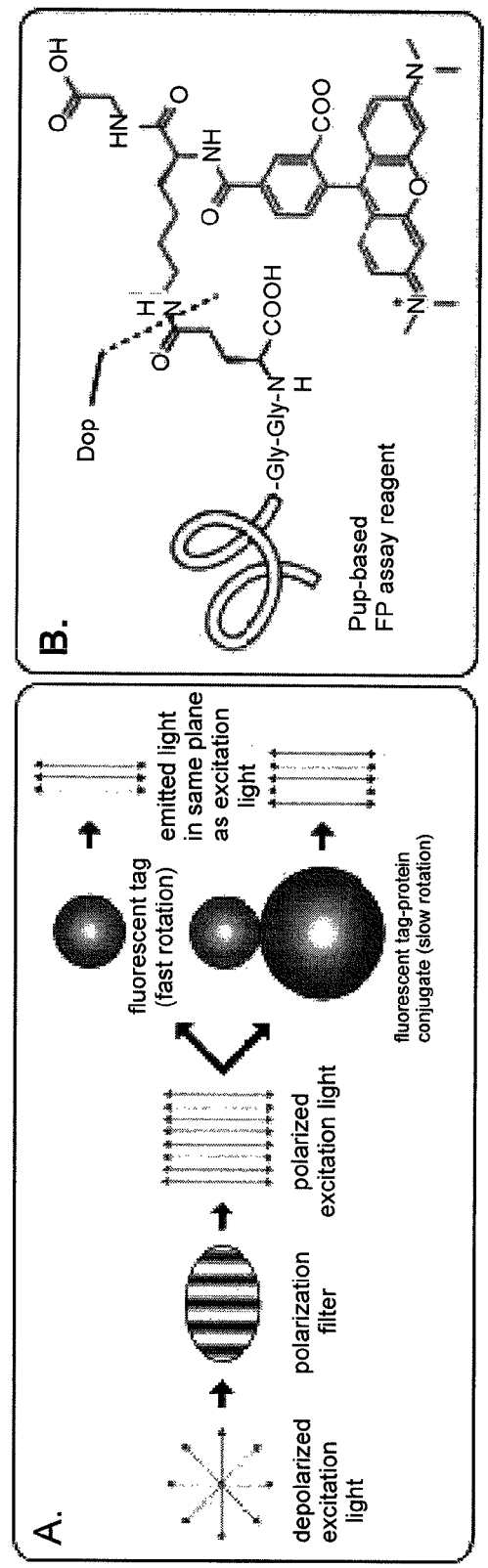

FIG. 7 shows (A) fluorescence polarization (FP) and (B) a Pup-based FP assay reagent Pup-Glu(TAMRA).

DETAILED DESCRIPTION OF THE INVENTION

In order to more clearly set forth the parameters of the present invention, the following definitions are used:

As used in this specification and the appended claims, the singular forms "a", "an", and "the" include plural references unless the context clearly dictates otherwise. Thus for example, reference to "the method" includes one or more methods, and/or steps of the type described herein and/or which will become apparent to those persons skilled in the art upon reading this disclosure.

The term "complementary" refers to two DNA strands that exhibit substantial normal base pairing characteristics. Complementary DNA may, however, contain one or more mismatches.

The term "hybridization" refers to the hydrogen bonding that occurs between two complementary DNA strands.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it is generally associated in its natural state (i.e., in cells or tissues). An isolated nucleic acid (either DNA or RNA) may further represent a molecule produced directly by biological or synthetic means and separated from other components present during its production.

The terms "percent similarity", "percent identity" and "percent homology" when referring to a particular sequence are used as set forth in the University of Wisconsin GCG software program and are known in the art.

The present invention also includes active portions, fragments, derivatives and functional or non-functional mimetics of a Pup of the invention. An "active portion" of a Pup means a peptide that is less than the full length Pup, but which retains measurable biological activity.

A "fragment" or "portion" of a Pup means a stretch of amino acid residues of at least about five to seven contiguous amino acids, often at least about seven to nine contiguous amino acids, typically at least about nine to thirteen contiguous amino acids and, most preferably, at least about twenty to thirty or more contiguous amino acids. A "derivative" of the Pup or a fragment thereof means a polypeptide modified by varying the amino acid sequence of the protein, e.g. by manipulation of the nucleic acid encoding the protein or by altering the protein itself. Such derivatives of the natural amino acid sequence may involve insertion, addition, deletion or substitution of one or more amino acids, and may or may not alter the essential activity of the original Pup.

The term "functional" as used herein implies that the nucleic or amino acid sequence is functional for the recited assay or purpose.

The term "functional fragment" as used herein implies that the nucleic or amino acid sequence is a portion or subdomain of a full length polypeptide and is functional for the recited assay or purpose.

The phrase "consisting essentially of" when referring to a particular nucleotide or amino acid means a sequence having the properties of a given SEQ ID No:. For example, when used in reference to an amino acid sequence, the phrase includes the sequence per se and molecular modifications that would not affect the basic and novel characteristics of the sequence.

A "replicon" is any genetic element, for example, a plasmid, cosmid, bacmid, phage or virus that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression vector" or "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the term "operably linked" refers to a regulatory sequence capable of mediating the expression of a coding sequence and which are placed in a DNA molecule (e.g., an expression vector) in an appropriate position relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Primers may be labeled fluorescently with 6-carboxyfluorescein (6-FAM). Alternatively primers may be labeled with 4, 7, 2', 7'-Tetrachloro-6-carboxyfluorescein (TET). Other alternative DNA labeling methods are known in the art and are contemplated to be within the scope of the invention.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like). "Mature protein" or "mature polypeptide" shall mean a polypeptide possessing the sequence of the polypeptide after any processing events that normally occur to the polypeptide during the course of its genesis, such as proteolytic processing from a polypeptide precursor. In designating the sequence or boundaries of a mature protein, the first amino acid of the mature protein sequence is designated as amino acid residue 1.

The term "tag", "tag sequence" or "protein tag" refers to a chemical moiety, either a nucleotide, oligonucleotide, polynucleotide or an amino acid, peptide or protein or other chemical, that when added to another sequence, provides additional utility or confers useful properties to the sequence, particularly with regard to methods relating to the detection or isolation of the sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules [e.g., hexahistidine epitope, flag epitope, c-myc epitope, transmembrane epitope of the influenza A virus hemaglutinin protein, protein A, cellulose binding domain, calmodulin binding protein, maltose binding protein, chitin binding domain, glutathione S-transferase, streptavidin ("Strep" tag) and the like] may be added to proteins to facilitate protein isolation by procedures such as affinity or immunoaffinity chromatography. Chemical tag moieties include such molecules as biotin, which may be added to either nucleic acids or proteins and facilitates isolation or detection by interaction with avidin reagents, and the like. Numerous other tag moieties are known to, and can be envisioned by, the trained artisan, and are contemplated to be within the scope of this definition.

As described herein, modified versions of Pup and functional fragments thereof (Pup and functional fragments thereof comprising a tag) are useful in methods for screening to identify modulators of Pup activity and/or enzymes, such as Dop, which are known to regulate Pup activity. Exemplary modified Pup molecules include full length Pup and functional fragments thereof linked to, for example, fluorophores or luminescent moieties (such, e.g., luciferin). The modified versions of Pup and functional fragments thereof differ in many respects from other labeled proteins. For the purposes of clarity, one of the pronounced structural distinctions is described here with respect to the attachment site for fluorescent labels, although it will be appreciated that other labels can be attached to Pup and functional fragments thereof at the same site and via the same or similar means. As described herein, modified versions of Pup and functional fragments thereof comprising fluorescent labels are linked through their C-terminal glutamic acid gamma carboxylate side chain to the fluorescent label. In contrast, fluorescently labeled ubiquitin and ubiquitin-like proteins, for example, are linked through the normal, alpha carboxylate C-terminus. With regard to the unusual linkage site described herein, the fluorescent moiety was not attached to the alpha carboxylate of the C-terminus of Pup since Dop reacts at the side chain, thereby converting a glutamine residue of free Pup into a glutamic acid residue, or hydrolyzing an isopeptide bond between the gamma carboxylate side chain of the Pup C-terminal glutamic acid and the epsilon amino group of a side chain lysine in a protein modified by Pup. It is noteworthy that the chemistry involved in attachment at the side chain is distinct from that required to attach a moiety to the normal C-terminus and novel synthetic methods were developed as described herein to generate the novel modified Pup molecules described herein. Exemplary modified Pups such as, for example, Pup(1-63)-Glu(AMC) and Pup(33-63)-Glu(AMC) are attached via the C-terminal glutamic acid side chain to the fluorogenic reporter moiety (AMC). Other reporter moieties such as a quenched rhodamine (fluorogenic) or lys(alphaTMR) can be linked via the C-terminal glutamic acid side chain of Pup or a functional fragment thereof to generate a modified Pup that can be used, for example, as a Pup-based DOP reporter in screening assays such as those described herein.

In addition to the embodiment set forth in the Examples, which involves direct coupling of the appropriate glutamic acid based building blocks to an appropriate synthetic Pup derivative, coupling via an appropriate Pup-thioester obtained by expression of a pup intein fusion is also envisioned herein. This is discussed in greater detail herein below.

Exemplary fluorophores of utility in the generation of modified versions of Pup and functional fragments thereof include, without limitation, fluorophores amino methyl coumarin (AMC), 5-tetramethylrhodamine (TAMRA), quenched rhodamine (e.g., rhodamine-110), lys[(alpha tetramethylrhodamine (TMR)], and amino trifluoromethyl coumarin (AFC). Fluorogenic substrates comprising AMC, AFC, or rhodamine-110 are derivatized with Pup on one of the amines and acylated on the other amino group. Linkage to fluorophores confers upon such modified Pup molecules a new and detectable property, whereby by virtue of the fluorescent read out that differs depending on whether the linkage to the fluorophore is intact or severed, the status of the linkage can be assessed. Accordingly, the linkage site to Pup or a fragment thereof can be chosen/designed such that attachment thereto or absence thereof reflects or is indicative of Dop activity, which in turn regulates Pup activity.

Indeed, in exemplary fashion, the present inventors selected the penultimate C-terminal amino acid for attachment of fluorophores because cleavage of the fluorophore from Pup or a functional fragment thereof at that site is indicative of the presence and activity Dop (deamidase of Pup). As indicated herein, Dop activates Pup prior to ligation to target proteins. More particularly, Dop catalyzes the deamidation of Pup's C-terminal glutamine to form a glutamate. Attachment of Pup occurs via the newly formed glutamyl side-chain carboxylate to the ε-amino moiety of a lysine residue of the target protein and is catalyzed by PafA, the Pup ligase. The pupylated proteins are then guided to the proteasome through the binding of Pup to Mpa (mycobacerial proteasome associated AAA ATPase), which unfolds proteins prior to delivery into the proteasome core (Striebel et al., *EMBO J* 2010, 29(7):1262-71; Burns et al. *J Bact* 192(11): 2933-35; Wang et al., *Nat Struct Mol Biol* 2010, 17 (11), 1352-1357). Dop can also function as a depupylase to remove and thereby recycle Pup from substrate proteins prior to proteasomal destruction (Burns et al., *Mol Cell* 2010, 39 (5), 821-827; Imkamp et al., *EMBO Rep* 2010, 11 (10), 791-797).

Figure 1:
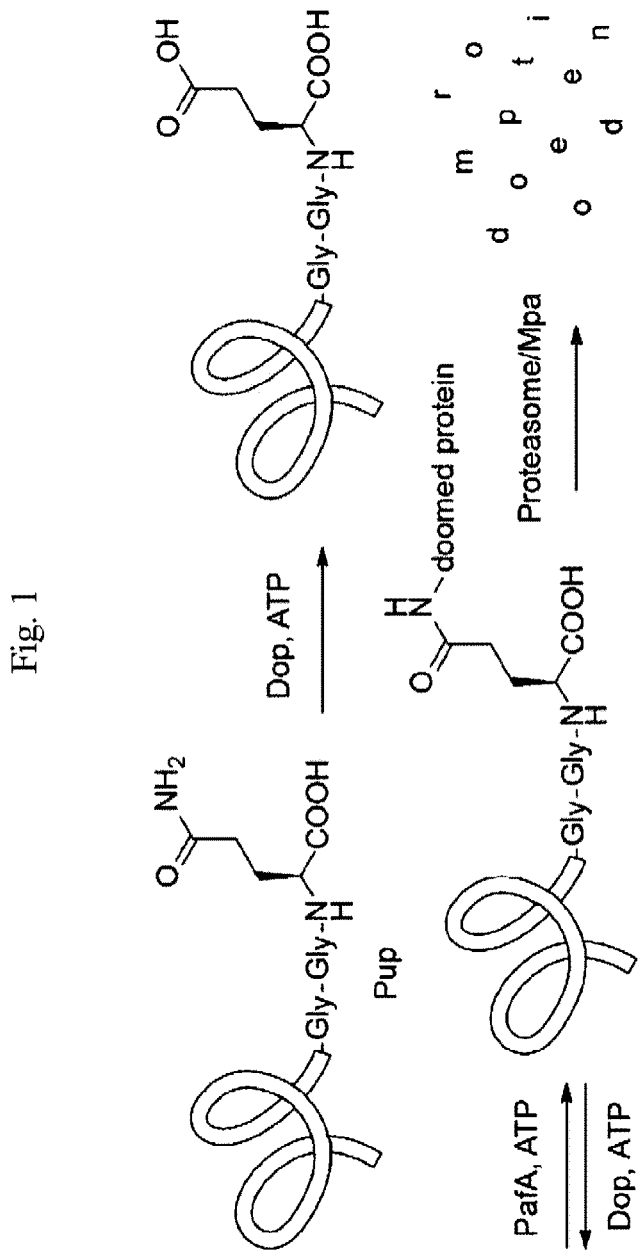
FIG. 1 shows Scheme 1: Pupylation pathway of the Pup—proteasome system (PPS) in *Mycobacterium tuberculosis* (Mtb).
Figure 2:
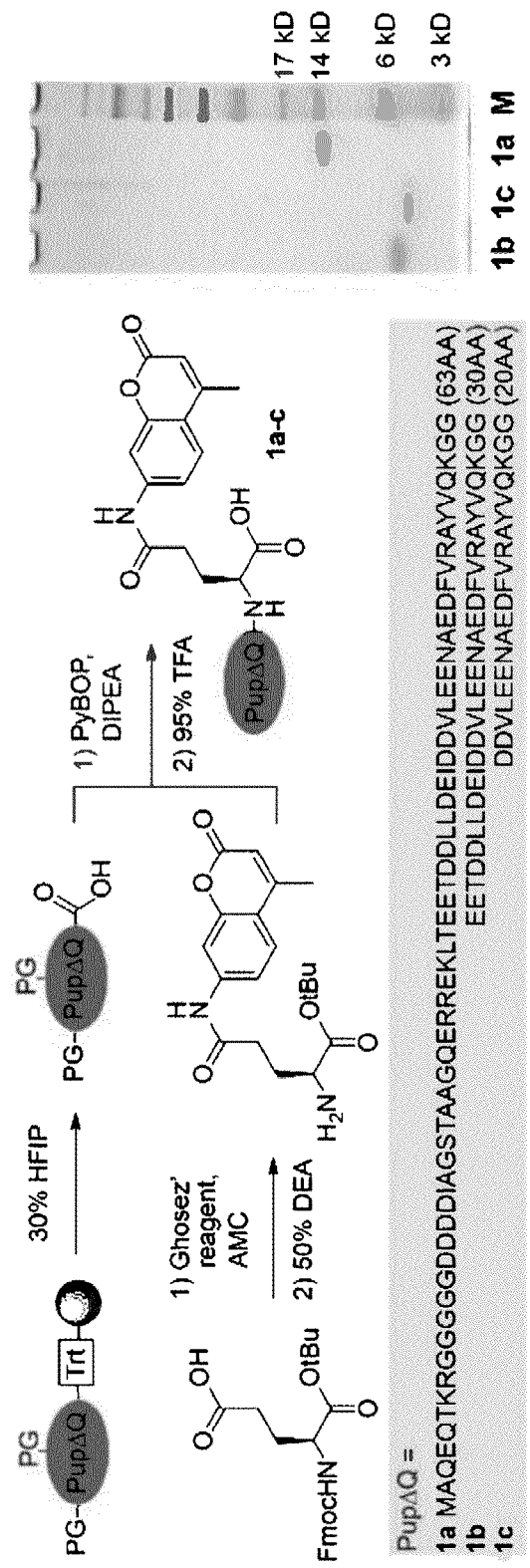
FIG. 2 shows Scheme 2: Chemical synthesis and SDS-page (12%) analysis of Pup-Glu(AMC) conjugates 1a-c. PG=protecting group; Trt=trityl; Fmoc=9-fluorenylmethyloxycarbonyl; HFIP=hexafluoroisopropanol; Ghosez'reagent=1-chloro-N,N,2-trimethyl-1-propenylamine; AMC=7-amino-4-methylcoumarin; DEA=diethylamine; PyBOP=benzotriazol-1-yl-oxytripyrrolidinophosphonium hexafluorophosphate; DIPEA=diisopropylamine; TFA=trifluoroacetic acid. Pup-Glu(AMC) conjugate 1a is referred to herein as SEQ ID NO: 5; Pup-Glu(AMC) conjugate 1b is referred to herein as SEQ ID NO: 6; and Pup-Glu(AMC) conjugate 1c is referred to herein as SEQ ID NO: 7).

In accordance with the above, modified Pup molecules can be used as Dop specific substrates or indicator molecules for Dop activity. Such modified Pup molecules are described herein and include: Pup(1-63)-Glu(AMC) (FIG. 2; Scheme 2: 1a); Pup(33-63)-Glu(AMC) (FIG. 2; Scheme 2: 1b); and Pup(1-64)-Lys(TAMRA) (FIG. 7).

As used herein, the term "Dop activity compatible buffer" refers to a buffer in which Dop is enzymatically active, preferably a buffer in which Dop activity is optimized. Such buffers comprise Dop; a Dop substrate, e.g., Pup(1-63)-Glu(AMC); ATP; $MgCl_2$; DTT; and NaCl in Tris pH 8 at suitable concentrations to promote Dop activity. An exemplary buffer is described in Example 1 herein below and comprises Dop; a Dop substrate, e.g., Pup(1-63)-Glu(AMC); 2.5 mM ATP; 20 mM $MgCl_2$; 1 mM DTT; and 50 mM NaCl in 50 mM Tris pH 8 to promote Dop activity.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. In other applications, the introduced nucleic acid may exist in the recipient cell or host organism only transiently.

A "clone" or "clonal cell population" is a population of cells derived from a single cell or common ancestor by mitosis or fission (with respect to bacteria).

A "cell line" is a clone of a primary cell or cell population that is capable of stable growth in vitro for many generations.

The compositions containing the molecules or compounds of the invention can be administered for diagnostic and/or therapeutic treatments. In therapeutic applications, compositions are administered to a patient already suffering from a disease or condition caused by or associated with a bacterial infection (such as, e.g., tuberculosis or leprosy) in an amount sufficient to cure or at least partially arrest the symptoms of the disease and its complications. An amount adequate to accomplish this is defined as a "therapeutically effective amount or dose." Amounts effective for this use will depend on the severity of the disease and the weight and general state of the patient.

An "immune response" signifies any reaction produced by an antigen, such as a protein antigen, in a host having a functioning immune system. Immune responses may be either humoral, involving production of immunoglobulins or antibodies, or cellular, involving various types of B and T lymphocytes, dendritic cells, macrophages, antigen presenting cells and the like, or both. Immune responses may also involve the production or elaboration of various effector molecules such as cytokines, lymphokines and the like. Immune responses may be measured both in in vitro and in various cellular or animal systems.

An "antibody" or "antibody molecule" is any immunoglobulin, including antibodies and fragments thereof, that binds to a specific antigen. The term includes polyclonal, monoclonal, chimeric, and bispecific antibodies. As used herein, antibody or antibody molecule contemplates both an intact immunoglobulin molecule and an immunologically active portion of an immunoglobulin molecule such as those portions known in the art as Fab, Fab', F(ab')2 and F(v).

As used herein, an "agent", "candidate compound", or "test compound" may be used to refer to, for example, nucleic acids (e.g., DNA and RNA), carbohydrates, lipids, proteins, peptides, peptidomimetics, small molecules and other drugs.

The term "control substance", "control agent", or "control compound" as used herein refers a molecule that is inert or has no activity relating to an ability to modulate a biological activity. With respect to the present invention, such control substances are inert with respect to an ability to modulate a Pup activity, and/or a signaling pathway that contributes to an activity of Pup, e.g., a proteasome degradation pathway. Exemplary controls include, but are not limited to, solutions comprising physiological salt concentrations.

The term "modulator of prokaryotic ubiquitin like protein (Pup) activity" as used herein refers to an agent that is capable of modulating (e.g., increasing or decreasing) an activity attributable to Pup. Such agents may work directly on Pup or indirectly, via modulating the activity of a component of the Pup-proteasome pathway (PPS) that, in turn, regulates Pup activity. In a particular embodiment, the agent modulates the activity of Dop, which is required to activate Pup. In a particular embodiment, the agent inhibits the activity of Dop, thereby inhibiting Pup activity. Methods for screening/identifying such agents are presented herein below.

As used herein, the term "proteasome substrate" is used to refer to polypeptides that are recognized and targeted for degradation by the proteasome. Proteasomes are large protein complexes found in all eukaryotes and archaea, as well as some bacteria. The main function of the proteasome is to degrade unneeded or damaged proteins by proteolysis, a chemical reaction that breaks protein bonds. Proteasomes are major components of the cellular machinery that enables cells to regulate the concentration of particular proteins and degrade misfolded proteins.

As used herein, the phrase "conjugated to proteasome substrates" refers to the covalent attachment of Pup to substrates. As exemplified herein, the covalent attachment of Pup to substrates may occur via an N-terminal peptide or isopeptide attachment of Pup to substrates. As further shown herein, covalent conjugation or attachment of Pup to a substrate serves to target the Pup-conjugated substrate for proteasome-mediated degradation. Conjugation to Pup is, therefore, associated with substrate degradation. With regard to Pup~Pup, Pup has lysines that could potentially be modified by other Pups in a manner analogous to ubiquitin.

Pup may also be involved in non-degradation associated modification, much like ubiquitin/SUMO that have been shown to modulate protein localization and activity.

As used herein "a change in the population of polypeptides covalently conjugated to Pup" refers to an increase or decrease in the amount of a particular polypeptide covalently conjugated to Pup or a difference in the spectrum polypeptides conjugated to Pup. With regard to the spectrum of polypeptides conjugated to Pup, this refers to the collection of different polypeptides conjugated to Pup that differ with respect to their primary amino acid sequences.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and described the methods and/or materials in connection with which the publications are cited.

Aspects Of The Invention

Before the present discovery and methods of use thereof are described, it is to be understood that this invention is not limited to particular assay methods, or test compounds and experimental conditions described, as such methods and compounds may vary. It is also to be understood that the terminology used herein is for the purpose of describing particular embodiments only, and is not intended to be limiting, since the scope of the present invention will be limited only the appended claims.

Mtb is one of the few bacterial species with a proteasome, a large protein complex that degrades proteins that cells have marked for destruction. The recently discovered Pup-proteasome pathway (PPS), also present in *Actinobacteria* and *Nitrospora*, is essential for the full virulence of Mtb in vivo (Pearce et al., *The EMBO J.* 2006, 25 (22), 5423-5432; Darwin et al., *Mol Microbiol* 2005, 55 (2), 561-571; Darwin et al., *Science* 2003, 302, 1963-1966; Gandotra et al., *PLoS Pathogens* 2010, 6 (8), e1001040; Pearce et al., *Science* 2008, 322 (5904), 1104-7; Cerda-Maira et al., *Mol Microbiol* 2010, 77 (5), 1123-1135). In this pathway, bacterial proteins are post-translationally modified with the small protein Pup (prokaryotic ubiquitin-like protein) to target them for degradation by the proteasome (Scheme 1; Burns et al., *Cell Microbiol* 2010, 12 (4), 424-431). Prior to ligation to target proteins, Pup is activated by Dop (deamidase of Pup). Dop catalyzes the deamidation of Pup's C-terminal glutamine to form a glutamate. Attachment of Pup occurs via the newly formed glutamyl side-chain carboxylate to the ϵ-amino moiety of a lysine residue of the target protein and is catalyzed by PafA, the Pup ligase. The pupylated proteins are then guided to the proteasome through the binding of Pup to Mpa (mycobacerial proteasome associated AAA ATPase), which unfolds proteins prior to delivery into the proteasome core composed of PrcA and PrcB subunits (Striebel et al., *EMBO J* 2010, 1-10; Wang et al., *Nat Struct Mol Biol* 2010, 17 (11), 1352-1357); Hu et al 2006 Mol Microbiol 59:1417-1426; Burns et al J Bact 2010 (supra). Dop can also function as a depupylase to remove and thereby recycle Pup from substrate proteins prior to proteasomal destruction (See Burns et al., *Mol Cell* 2010, 39 (5), 821-827; Imkamp et al., *EMBO Rep* 2010, 11 (10), 791-797; the entire content of each of which is incorporated herein in its entirety). All six proteins are required for a functional Pup-proteasome system in bacteria.

Proteasomes are found in all eukaryotic cells, including human cells. Here, proteins are targeted for proteasomal degradation by post-translational modification with a 76 amino acid protein: ubiquitin (Ub). The reversible covalent attachment of Ub occurs typically through an isopeptide bond between the C-terminal carboxylate of Ub and the ε-amino moiety of a lysine side chain in the target protein or in Ub itself. The Ub-proteasome system (UPS) is well-studied and essential to normal cell function; therefore the enzymes of this pathway are recognized as attractive drug targets for various diseases (Bedford et al., *Nat Rev Drug Discovery* 2011, 10 (1), 29-46).

Despite the functional homology and analogous mechanism of the PPS and UPS, the homology among individual proteins between the systems is limited. Most notably, Dop and PafA appear to be unique to bacteria with no known sequence homologs in eukaryotes. Dop and PafA are homologous proteins with similarity to the γ-glutamyl cysteine ligase family of proteins (Iyer et al., 2008, Biology Direct 3:45). PafA catalyzes pupylation in an ATP-dependent reaction, where the gamma carboxylate of Pup's C-terminal glutamate is phosphorylated prior to attack by a substrate lysine. Interestingly, Dop requires ATP binding but not hydrolysis to catalyze deamidation or depupylation (Striebel et al., 2009, Nat Struct Mol Biol 16:647-651; the entire content of which is incorporated herein by reference). Because the PPS is critical for Mtb to cause lethal infections and at least two enzymes in this pathway are unique to bacteria, they provide ideal targets for the development of selective chemotherapies against Mtb. The viability of this approach has recently been demonstrated by the identification of oxathiazol-2-one compounds as selective proteasome inhibitors for a non-replicating population of Mtb (Lin et al., *Nature* 2009, 461 (621-626)).

Since Dop is required for the full virulence of Mtb (Cerda-Maira et al., *Mol Microbiol* 2010, 77 (5), 1123-1135), the identification of inhibitors against Dop could lead to potential anti-TB lead compounds. However, not much is known about the mechanism of Dop activity and the identification of drug-like inhibitors requires well-designed high throughput screening (HTS) assay reagents that were not available in advance of the HTS reagents described herein which were made using a novel synthetic chemistry protocol as described herein. Presently, a typical Dop assay consists of manual time points and analysis of reaction products by SDS-PAGE or immunoblotting, an inefficient and unquantitative method to measure activity. In light of the above limitations, the present inventors investigated the development of fluorogenic assay reagents to probe for Dop activity and for use in Dop inhibitor screens. Various exemplary fluorogenic assay reagents and methods of making same are presented herein.

Further to the above, the identification of Pup has led to the generation of reagents, such as modified forms of Pup and functional fragments thereof that are useful for screening assays directed to the identification of compounds that modulate Pup activity or modulate the activity of enzymes that contribute to Pup activity, such as Dop. Such enzymes may be involved in the conjugation of Pup to substrates (pupylation) or enzymes required for de-pupylating (removal of conjugated Pup) from substrates. Screening assays may, for example, be cell-based or test-tube based screening assays as described herein in greater detail. See, for example, Example I presented herein. Moreover, methods and agents useful for modulating Pup activity and prokaryotic proteasome activity may be used to advantage as targeted therapeutics for the treatment of diseases associated with bacterial infections. More particularly, it is envisioned that agents identified using the method of the present invention may be useful for the treatment of patients with, for example, tuberculosis or leprosy.

A skilled practitioner would be aware that the literature provides details pertaining to numerous additional assays that may be used in conjunction with the present invention. One such reference is U.S. Pat. No. 7,282,491, the content of which is incorporated herein in its entirety.

Further to the above, an isolated nucleic acid sequence that encodes a polypeptide comprising SEQ ID NO: 2 or a functional fragment thereof is presented herein. Also of utility in the present methods are expression vectors comprising an isolated nucleic acid sequence which encodes a polypeptide comprising SEQ ID NO: 2 or a functional fragment thereof. Cells comprising these expression vectors are also envisioned.

In another aspect, an isolated amino acid sequence comprising a polypeptide of SEQ ID NO: 2 or a functional fragment thereof is presented. Also included are expression vectors encoding an amino acid sequence of the invention, wherein expression of the amino acid sequence is controlled by regulatory sequences in the expression vector, cells comprising such expression vectors, and transgenic animals comprising an amino acid sequence of the invention, wherein the amino acid sequence is expressed in at least one cell in the transgenic animal.

In another aspect, an isolated nucleic acid sequence comprising SEQ ID NO: 1, wherein the nucleic acid sequence encodes Pup or a functional fragment thereof, is presented. An expression vector comprising a nucleic acid sequence of SEQ ID NO: 1, wherein the nucleic acid sequence encodes Pup or a functional fragment thereof, and SEQ ID NO: 1 is operably linked to a regulatory sequence is also described. Moreover, a cell comprising such an expression vector comprising a nucleic acid sequence of SEQ ID NO: 1 is presented. In another aspect, a transgenic animal comprising a nucleic acid sequence comprising SEQ ID NO: 1, wherein the nucleic acid sequence encodes Pup or a functional fragment thereof, and wherein the nucleic acid sequence is expressed in at least one cell of the transgenic animal, is presented.

Methods of Tuberculosis (TB) Therapy

*Mycobacteria* are aerobic and nonmotile bacteria that are characteristically acid-alcohol fast. The exception to this rule is the species *Mycobacterium marinum* which has been shown to be motile within macrophages. All *Mycobacterium* species share a characteristic cell wall, thicker than in many other bacteria, which is hydrophobic, waxy, and rich in mycolic acids/mycolates. The cell wall thus presents challenges with respect to delivery of therapeutics that are capable of permeating the cell wall.

It is well recognized that Mycobacterial infections are notoriously difficult to treat. The organisms are resistant to therapeutics at least in part due to their cell wall, which is neither truly Gram negative nor positive, and unique to the family. Moreover, *Mycobacteria* are naturally resistant to a number of antibiotics, such as penicillin, that destroy cell walls. The presence of the hydrophobic, waxy cell wall also enables *Mycobacteria* to survive prolonged exposure to acids, alkalis, detergents, oxidative bursts, lysis by complement and antibiotics, which naturally leads to antibiotic resistance. Most *Mycobacteria* are, however, susceptible to the antibiotics clarithromycin and rifamycin, but antibiotic-resistant strains are known to exist. The therapeutic agents identified using the methods of the present invention are envisioned as useful for both treatment of antibiotic-sensitive strains and antibiotic-resistant strains. Moreover, therapeutic agents identified using the present methods may be used in conjunction with known antibiotics, including clarithromycin and rifamycin. As described by Barrow et al. (Antimicrobial Agents and Chemotherapy 42:2682-2689, 1998), the entire contents of which is incorporated herein in its entirety, microsphere technology has been used to develop formulations of rifamycin to achieve targeted delivery to macrophages. A skilled practitioner would, therefore, appreciate that similar technology may be applied with respect to administration of agents identified using the methods of the present invention.

With respect to the complications associated with delivery, objectives involved with the development of candidate therapeutics include the identification and generation of compounds, such as, for example, small molecules that inhibit enzymes in the pupylation pathway. Transport of small molecules through the cell wall is more readily achieved than larger molecules.

Preparation of Pup-Encoding Nucleic Acid Molecules and Pup

Nucleic Acid Molecules: Nucleic acid molecules encoding Pup may be prepared by two general methods: (1) Synthesis from appropriate nucleotide triphosphates; or (2) Isolation from biological sources. Both methods utilize protocols well known in the art.

The availability of nucleotide sequence information, such as a full length DNA of SEQ ID NO: 1 (See FIG. 5), enables preparation of an isolated nucleic acid molecule of the invention by oligonucleotide synthesis. Synthetic oligonucleotides may be prepared by the phosphoramidite method employed in the Applied Biosystems 380A DNA Synthesizer or similar devices. The resultant construct may be purified according to methods known in the art, such as high performance liquid chromatography (HPLC). Double-stranded polynucleotides, such as a DNA molecule of the present invention, may be synthesized in stages, due to the size limitations inherent in oligonucleotide synthetic methods. Synthetic DNA molecules constructed by such means may then be cloned and amplified in an appropriate vector. Nucleic acid sequences encoding Pup may be isolated from appropriate biological sources using methods known in the art. In that most bacterial genomes of interest have been completely sequenced, or will be in the near future, regular PCR off genomic DNA is typically used to isolate full length sequences. In an alternative embodiment, utilizing the sequence information provided by the full length DNA sequence, genomic clones encoding Pup may be isolated.

Nucleic acids of the present invention may be maintained as DNA in any convenient cloning vector. In a preferred embodiment, clones are maintained in a plasmid cloning/expression vector, such as pBluescript (Stratagene, La Jolla, Calif.), which is propagated in a suitable *E. coli* host cell.

Pup-encoding nucleic acid molecules of the invention include DNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of a DNA of SEQ ID NO: 1. Such oligonucleotides are useful as probes for detecting or isolating genes related to Pup and in polymerase chain reaction (PCR) amplifications.

The present invention provides a method of obtaining a nucleic acid of interest, the method including hybridization of a probe having part or all of the sequence shown in SEQ ID NO: 1, or a complementary sequence thereto, to target nucleic acid. Successful hybridization leads to isolation of nucleic acid which has hybridized to the probe, which may involve one or more steps of PCR amplification.

In some preferred embodiments, oligonucleotides according to the present invention that are fragments of the sequences shown in SEQ ID NO: 1 are at least about 10 nucleotides in length, more preferably at least 15 nucleotides in length, more preferably at least about 20 nucleotides in length. Such fragments themselves individually represent aspects of the present invention. Fragments and other oligonucleotides may be used as primers or probes as discussed but may also be generated, e.g., by PCR.

Polypeptides: Pup is the first prokaryotic ubiquitin-like protein to be identified. Indeed, Pup is the first known post-translational protein modifier to be identified in bacteria. As described herein, the identification of Pup has led to the generation of reagents, such as modified forms of Pup and functional fragments thereof that are useful for screening assays directed to the identification of agents/compounds that modulate Pup activity or modulate the activity of enzymes that contribute to Pup activity, such as Dop. Such enzymes may be involved in the conjugation of Pup to substrates (pupylation) or enzymes required for de-pupylating (removal of conjugated Pup) from substrates. Agents identified using such screens that can modulate (e.g., inhibit) Pup activity and prokaryotic proteasome activity may be used to advantage as targeted therapeutics for the treatment of diseases associated with bacterial infections. The targeted nature of such agents is underscored by the fact that the Pup-proteasome pathway (PPS) is essential for Mtb-mediated lethal infections and at least two enzymes in this pathway are unique to bacteria. In particular embodiments, it is envisioned that agents identified using the method of the present invention may be useful for the treatment of patients with, for example, tuberculosis or leprosy.

A full-length Pup of the present invention may be prepared in a variety of ways, according to known methods. The protein may be purified from appropriate sources. This is not, however, a preferred method due to the low amount of protein likely to be present in a given cell type at any time. The availability of nucleic acid molecules encoding Pup enables production of this protein using in vitro expression methods known in the art. For example, a DNA or gene may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega Biotech, Madison, Wis. or BRL, Rockville, Md.

It is, however, noteworthy that Pup expresses well in *E. coli* using pET24(b)+ (Novagen).

Alternatively, according to a preferred embodiment, larger quantities of Pup may be produced by expression in a suitable prokaryotic or eukaryotic system. For example, part or all of a DNA molecule, such as the sequence of SEQ ID NO: 1, may be inserted into a plasmid vector adapted for expression in a bacterial cell, such as *E. coli*. Such vectors comprise regulatory elements necessary for expression of the DNA in a host cell (e.g. *E. coli*) positioned in such a manner as to permit expression of the DNA in the host cell. Such regulatory elements required for expression include promoter sequences, transcription initiation sequences and, optionally, enhancer sequences.

Pup produced by gene expression in a recombinant prokaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope or the hemagglutinin epitope. Such methods are commonly used by skilled practitioners.

Pup and fragments thereof prepared by the aforementioned methods, may be analyzed according to standard procedures. For example, such proteins may be subjected to amino acid sequence analysis, according to known methods.

Polypeptides which are amino acid sequence variants, alleles, derivatives or mutants are also provided by the present invention. A polypeptide which is a variant, allele, derivative, or mutant may have an amino acid sequence that differs from that given in SEQ ID NO: 2 by one or more of addition, substitution, deletion and insertion of one or more amino acids. Preferred such polypeptides have Pup function, that is to say have one or more of the following properties: the ability to be conjugated to proteasome substrates, whereby conjugation serves to target the substrate for proteasome-mediated degradation; immunological cross-reactivity with an antibody reactive with the polypeptide for which the sequence is given in SEQ ID NO: 2; sharing an epitope with the polypeptide for which the sequence is given in SEQ ID NO: 2 (as determined for example by immunological cross-reactivity between the two polypeptides.

Antibodies that are specific for Pup have been characterized, as have methods of making same. See, for example United States Patent Application Serial Number 2010/0055715; Pearce et al. 2008 Science 322:1104-1107; Burns et al. 2010 J Bact 192(11):2933-35; Burns et al. 2010 *Mol Cell* 39 (5), 821-827; Festa et al. 2010 PLoS ONE 5:e8589; Cerda-Maira et al 2010 Mol Microbiol 77:1123-1135; Cerda-Maira et al 2011 EMBO 12:863-870; Imkamp et al 2010 Mol Microbiol 75:744-754; and Imkamp et al., *EMBO Rep* 2010, 11 (10), 791-797), the entire content of each of which is incorporated herein in its entirety.

A polypeptide which is an amino acid sequence variant, allele, derivative or mutant of the amino acid sequence shown in SEQ ID NO: 2 may comprise an amino acid sequence which shares greater than about 35% sequence identity with the sequence shown, greater than about 40%, greater than about 50%, greater than about 60%, greater than about 70%, greater than about 80%, greater than about 90% or greater than about 95%. Particular amino acid sequence variants may differ from that shown in SEQ ID NO: 2 by insertion, addition, substitution or deletion of 1 amino acid, 2, 3, 4, 5-10, 10-20, 20-30, 30-40, or 40-50 amino acids. For amino acid "homology", this may be understood to be identity or similarity (according to the established principles of amino acid similarity, e.g., as determined using the algorithm GAP (Genetics Computer Group, Madison, Wis.). GAP uses the Needleman and Wunsch algorithm to align two complete sequences that maximizes the number of matches and minimizes the number of gaps. Generally, the default parameters are used, with a gap creation penalty=12 and gap extension penalty=4. Use of GAP may be preferred but other algorithms may be used including without limitation, BLAST (Altschul et al. (1990 J. Mol. Biol. 215:405-410); FASTA (Pearson and Lipman (1998) PNAS USA 85:2444-2448) or the Smith Waterman algorithm (Smith and Waterman (1981) J. Mol. Biol. 147:195-197) generally employing default parameters.

Use of either of the terms "homology" and "homologous" herein does not imply any necessary evolutionary relationship between the compared sequences. The terms are used similarly to the phrase "homologous recombination", i.e., the terms merely require that the two nucleotide sequences are sufficiently similar to recombine under appropriate conditions.

A polypeptide according to the present invention may be used in screening assays for molecules which affect or modulate Pup activity or function. Such molecules may be useful for research purposes.

Methods for Synthesizing Modified Pup and Functional Fragments Thereof

Synthesis of Peptides 1a-c

The PupΔQ sequence was synthesized on a pre-loaded Fmoc amino acid trityl resin (0.2 mmol/g) at 25 µmol scale, using fourfold excess of appropriately side chain protected Fmoc-amino acids in N-methylpyrrolidinone (NMP) relative to the resin, PyBOP (4 equiv) and DIPEA (8 equiv) were used as condensing reagents. Fmoc removal was carried out using 20% piperidine in NMP for 2×2 and 1×5 min and capping of the resin was performed with a mixture of $Ac_2O$/DIPEA/HOBt in NMP at 500 mM, 125 mM and 15 mM respectively (3×1.2 mL, 2×2 and 1×5 min). During the synthesis different coupling protocols were used; coupling cycle 1-30: single couplings of 40 min, double couplings of 2×40 min for cycles 21, 22, 24 and 28, no capping; coupling cycle 31-39: single couplings of 60 min, double couplings of 2×60 min for cycles 33, 34, 38 and 39, no capping; coupling cycle 40-61: single couplings of 60 min, double couplings of 2×60 min for cycles 40, 42, 46, 48, 51-54, 58 and 59, capping after each coupling cycle. During the chain elongation, dipeptide pseudoproline building blocks were incorporated at positions 21/22 (Fmoc-Ser-Thr($\Psi^{Me,Me}$pro)-OH) and 32/33 (Fmoc-Leu-Thr ($\Psi^{Me,Me}$pro)-OH. After completion of the solid phase peptide synthesis, the resin was washed with $Et_2O$, dried under high vacuum and stored for further use.

Then, the resin bound polypeptide was treated with 5 mL of dichloromethane (DCM)/1,1,1,3,3,3-hexafluoropropane-2-ol (hexafluoroisopropanol) (HFIP) (7:3 v/v) for 30 min and filtered. This DCM/HFIP treatment was repeated once more and the resin was rinsed with DCM (3×5 mL). The combined filtrates were concentrated, co-evaporated with DCM and dried under high vacuum. The partially protected peptide residue (1 equiv) was redissolved in DCM and reacted with H-Glu(AMC)-OtBu (45 mg, 125 µmol, 5 equiv) in the presence of PyBOP (65 mg, 125 µmol, 5 equiv) and TEA (35 µL, 250 µmol, 10 equiv). The reaction mixture was stirred over night at room temperature. The volatiles were removed in vacuo and the residue was treated with TFA/$H_2O$/TiS (95:2.5: 2.5 v/v/v) for 3 h followed by precipitation with cold $Et_2O$/pentane (3:1 v/v). The precipitated crude protein was washed with $Et_2O$/pentane (3:1 v/v, once) and $Et_2O$ (twice). Finally, the pellet was dissolved in a mixture of $H_2O$/$CH_3CN$/HOAc (65/25/10 v/v/v) and lyophilized. The crude product was purified by preparative HPLC on a Waters Atlantis prep T3™ (10×150 mm, 5 µm) column, using 2 mobile phases: A=0.1% TFA in water and B=0.1% formic acid in $CH_3CN$ with the following gradient: 0-5 min: 5% B; 5-8 min:→25% B; 8-30 min:→60% B; 30-33 min:→95% B; 33-35 min: 95% B.

MAQEQTKRGGGGGDDDDIAGSTAAGQER-REKLTEETDDLLDEIDDV LEENAEDFVRAYVQKGG-Glu(AMC) (1a; SEQ ID NO: 5). Yield: 4.3 mg (4%), $R_t$: 7.08 min (analytical HPLC-MS was performed on a Waters Alltima C18 (2.1×100 mm, 3 µM) column using 2 mobile phases: A=0.1% formic acid in water and B=0.1% formic acid in $CH_3CN$ under the following conditions: flow rate=0.4 mL/min, runtime =20 min, column T=40° C. Gradient: 0-1 min: 5% B; 1-11 min:→95% B; 11-16 min: 95% B), MS ES+ (amu) calculated: 7098 [M]. found 7099 [M+H]+.

EETDDLLDEIDDVLEENAEDFVRAYVQKGG-Glu (AMC) (1b; SEQ ID NO: 6). Yield: 2.1 mg (5%), R$_t$: 7.78 min (analytical HPLC-MS was performed in the same fashion as for 1a), MS ES+ (amu) calculated: 3711 [M]. found 3711 [M+H]+.

DDVLEENAEDFVRAYVQKGG-Glu(AMC) (1c; SEQ ID NO: 7). Yield: 4.3 mg (4%), R$_t$: 6.62 min (analytical HPLC-MS was performed in the same fashion as for 1a), MS ES+ (amu) calculated: 2538 [M]. found 2539 [M+H]+.

H-Glu(AMC)-OtBu: Synthetic details on the preparation of H-Glu(AMC)-OtBu and characterization data are included herein below.

Uses of Pup-Encoding Nucleic Acids and Pup Polypeptides

As indicated herein, Pup nucleic acids and proteins and modified versions thereof may be used as research tools to identify modulators of Pup activity or modulators of pathways that regulate Pup activity. Modulators so identified may prove to be suitable therapeutics for use in the treatment of patients (e.g., humans) afflicted with a bacterial disease.

Accordingly, Pup nucleic acids and proteins and modified versions thereof may be used in a variety of methods described herein, such as a method for identifying modulators of Pup activity (in a bacterial cell or in a test tube); a method for identifying modulators of an enzyme that covalently attaches Pup to a proteasome substrate in a bacterial cell (which may be referred to herein as activation and conjugation enzymes of Pup); and/or a method for identifying modulators of an enzyme that de-pupylates substrate proteins prior to proteasomal destruction.

Pup nucleic acids (and vectors comprising same) proteins and modified versions thereof may also be used in compositions.

Pup nucleic acids (and vectors comprising same) and proteins and modified versions thereof may also be components in kits. An exemplary kit is described herein for screening to identify modulators of Pup activity and modulators of enzymes that regulate Pup activity.

Moreover, the synthesis of Pup-traps, for example, is expected to lead to the development of therapeutics for the treatment of diseases caused by bacterial infections. As indicated herein, the synthesis of Pup-traps involves the production of recombinant Pup in E. coli, which is chemically modified at the C-terminus with a moiety like 6-Diazo-5-oxo-L-norleucine (DON) or acivicin.

Pup-Encoding Nucleic Acids: Pup-encoding nucleic acids may be used for a variety of purposes in accordance with the present invention. Pup-encoding DNA, RNA, or fragments thereof may be used as probes to detect the presence of and/or expression of genes encoding Pup-like proteins. Methods in which Pup-encoding nucleic acids may be utilized as probes for such assays include, but are not limited to: (1) in situ hybridization; (2) Southern hybridization (3) northern hybridization; and (4) assorted amplification reactions such as PCR.

Nucleic acid molecules, or fragments thereof, encoding Pup may also be utilized to control the production of Pup, thereby regulating the amount of protein available to participate in pupylation. Alterations in the physiological amount of Pup protein may dramatically affect the activity of other protein factors involved in protein degradation.

From the foregoing discussion, it can be seen that Pup-encoding nucleic acids and Pup expressing vectors can be used to produce large quantities of Pup and modified Pup and modified Pup can be used to advantage in screening assays to identify modulators of Pup activity that act via direct and indirect means.

Structural Features of Pup and Significance Thereof in Identifying Compounds Capable of Modulating Pup Activity Suitable peptide targets in Pup include, but are not limited to, those residues and regions listed below. Suitable peptide targets in Pup include the C-terminus, which is significant because it conjugates to substrates and interacts with Mpa (the ATPase) as demonstrated by a two hybrid screen and co-purification. See Pearce et al. (2008 Science 322:1104-1107). Also included are critical residues and small peptides encompassing these critical residues (e.g. 5-10 residue peptides comprising these residues and flanking residues thereof) which are identified on the basis of high resolution information determined for Pup. Along these lines, the highly conserved penultimate di-glycine is maintained in all ubiquitin-like proteins characterized to date and cannot be mutated or moved in Pup without loss of optimal activity.

Agents Identified by the Screening Methods of the Invention

The invention provides methods for identifying agents (e.g., candidate compounds or test compounds) that modulate Pup activity. Agents identified by the screening method of the invention are useful as candidate anti-tuberculosis and/or anti-leprosy therapeutics.

Examples of agents, candidate compounds or test compounds include, but are not limited to, nucleic acids (e.g., DNA and RNA), carbohydrates, lipids, proteins, peptides, peptidomimetics, small molecules and other drugs. Exemplary nucleic acids determined to be capable of modulating Pup activity include, but are not limited to: Pup siRNA molecules. Agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) Anti-cancer Drug Des. 12:145; U.S. Pat. Nos. 5,738,996; and 5,807,683, each of which is incorporated herein in its entirety by reference).

Examples of methods for the synthesis of molecular libraries can be found in the art, for example in: DeWitt et al. (1993) Proc. Natl. Acad. Sci. USA 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233, each of which is incorporated herein in its entirety by reference.

Libraries of compounds may be presented, e.g., presented in solution (e.g., Houghten (1992) Bio/Techniques 13:412-421), or on beads (Lam (1991) Nature 354:82-84), chips (Fodor (1993) Nature 364:555-556), bacteria (U.S. Pat. No. 5,223,409), spores (U.S. Pat. Nos. 5,571,698; 5,403,484; and 5,223,409), plasmids (Cull et al. (1992) Proc. Natl. Acad. Sci. USA 89:1865-1869) or phage (Scott and Smith (19900 Science 249:386-390; Devlin (1990) Science 249:404-406; Cwirla et al. (1990) Proc. Natl. Acad. Sci. USA 87:6378-6382; and Felici (1991) J. Mol. Biol. 222:301-310), each of which is incorporated herein in its entirety by reference.

Screening Assays

In one embodiment, compounds/agents (e.g., small molecules) that modulate Pup activity are identified in a cell-free assay system. In accordance with this embodiment, a modified Pup or modified fragment thereof is contacted with a candidate compound or a control compound and the ability of the candidate compound to modulate Pup activity is determined. If desired, this assay may be used to screen a plurality (e.g. a library) of candidate compounds. In one embodiment, modified Pup or a modified fragment thereof is first immobilized, by, for example, contacting with an immobilized antibody which specifically recognizes and binds to Pup, or by contacting a purified preparation of modified Pup or modified fragment thereof, with a surface designed to bind proteins. Modified Pup or a modified fragment thereof may be partially or completely purified (e.g., partially or completely free of other polypeptides) or part of a cell lysate. Further, modified Pup or a modified fragment thereof may be part of a fusion protein comprising Pup or a biologically active portion thereof, and a domain such as glutathionine-S-transferase. Alternatively, modified Pup or a modified fragment thereof can be biotinylated using techniques well known to those of skill in the art (e.g., biotinylation kit, ThermoScientific; Rockford, Ill.). The ability of the candidate compound to modulate Pup activity can be determined by detection methods known to those of skill in the art.

In an embodiment thereof, a modified Pup or a functional fragment thereof is used in the screening assays described herein. In a particular embodiment, such modified Pup or a functional fragment thereof comprises a C-terminus modification. In a more particular embodiment, the C-terminus modification is a fluorescent moiety. Exemplary fluorescent moieties include: amino methyl coumarin (AMC); 5-tetramethylrhodamine (TAMRA), quenched rhodamine (e.g., rhodamine-110), lys[(alpha tetramethylrhodamine (TMR)], and amino trifluoromethyl coumarin (AFC). As described herein, exemplary modified Pup or a functional fragment thereof comprising a fluorescent moiety include: Pup(1-63)-Glu-AMC) (1a), Pup(33-63)-Glu-AMC) (1b), and Pup(1-64)-Lys-TAMRA. With regard to fluorescent conjugates of Pup, such as, e.g., Pup(1-63)-Glu-AMC, the ability of an agent or compound to modulate Pup activity or the PPS is evaluated based on the difference in fluorescence readout in the presence or absence of the agent/compound. Typically, contacting fluorescent conjugates of Pup in the presence of Dop under conditions suitable or compatible with Dop activity detection of an increase in fluorescence is indicative of conditions General Fmoc SPPS Strategy SPPS was performed on a Syro II MultiSyntech Automated Peptide synthesizer using standard 9-fluorenylmethoxycarbonyl (Fmoc) based solid phase peptide chemistry at 25 µmol scale, using fourfold excess of amino acids in NMP relative to pre-loaded Fmoc amino acid trityl resin (0.2 mmol/g, Rapp Polymere GmbH), PyBOP (4 equiv) and DIPEA (8 equiv) were used as condensing reagents. All amino acids were Fmoc protected, except for the final N-terminal amino acids which were introduced as the corresponding Boc derivative. The following protected amino acid and pseudoproline dipeptide building blocks were used during Pup synthesis: Fmoc-L-Ala-OH, Fmoc-L-Arg-(Pbf)-OH, Fmoc-L-Asn (Trt)-OH, Fmoc-L-Asp(OtBu)-OH, Fmoc-L-Gln(Trt)-OH, Fmoc-L-Glu(OtBu)-OH, Fmoc-L-Gly-OH, Fmoc-L-Ile-OH, Fmoc-L-Leu-OH, Fmoc-L-Lys(Boc)-OH, Fmoc-L-Phe-OH, Fmoc-L-Ser(tBu)-OH, Fmoc-L-Thr(tBu)-OH, Fmoc-L-Tyr(tBu)-OH, Fmoc-L-Val-OH, Boc-L-Asp(OtBu)-OH, Boc-L-Glu(OtBu)-OH, Boc-L-Met-OH, Fmoc-Ser-Thr($\Psi^{Me,Me}$pro)-OH) and Fmoc-Leu-Thr($\Psi^{Me,Me}$pro)-OH. All amino acid and dipeptide building blocks were dried under high vacuum overnight prior to use. Fmoc removal was carried out using 20% piperidine in NMP for 2×2 and 1×5 min. Capping of the resin was performed with a mixture of $Ac_2O$/DIPEA/HOBt in NMP at 500 mM, 125 mM and 15 mM respectively (3×1.2 mL, 2×2 and 1×5 min). This solution was prepared freshly on ice every 2 days.

Coupling cycle 1-30:
Single couplings of 40 min
Double couplings of 2×40 min only for cycles 21, 22, 24 and 28
No capping
Coupling cycle 31-39:
Single couplings of 60 min
Double couplings of 2×60 min only for cycles 33, 34, 38 and 39
No capping
Coupling cycle 40-61
Single couplings of 60 min
Double couplings of 2×60 min only for cycles 40, 42, 46, 48, 51-54, 58 and 59
Capping after each coupling cycle After completion of the synthesis, the resin was washed with $Et_2O$, dried under high vacuum and stored for further use.

Use of Dipeptide Pseudoproline Building Blocks

Three Pup(1-63) sequences were synthesized using one, two or no pseudoproline dipeptide building block(s) and the crude products were analyzed by SDS page.

Synthesis of H-Glu-OtBu

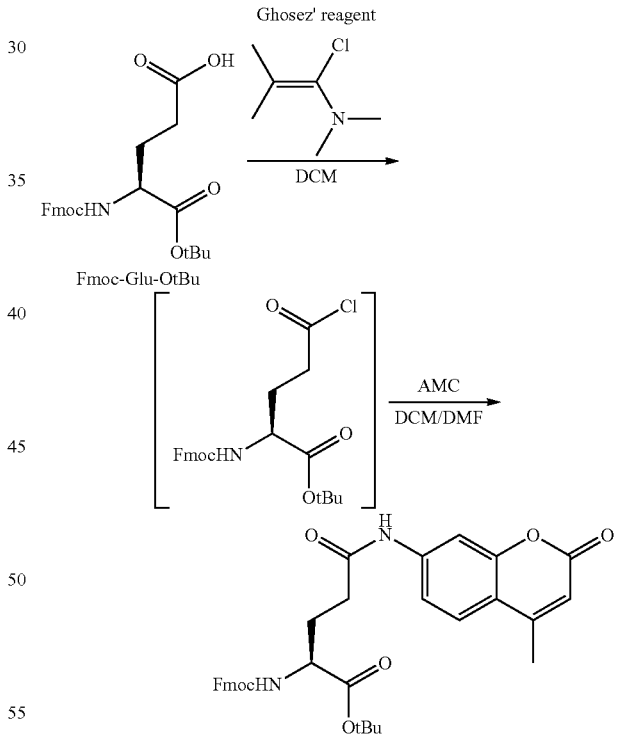

Fmoc-Glu(AMC)-OtBu (2). Under argon, 1-Chloro-N,N,2-trimethyl-1-propenylamine (Ghosez' reagent) (440 µL, 3.3 mmol) was added to a cooled (0° C.) and stirred solution of Fmoc-Glu(AMC)-OtBu (700.0 mg, 1.6 mmol) in dry DCM (10 mL). The resulting mixture was immediately transferred to a separate flask containing a stirred solution of AMC (316.0 mg, 1.8 mmol) in dry DMF (40 mL) and the resulting mixture was stirred at room temperature under argon. After 16 h an extra portion of the Ghosez' reagent (220 µL, 1.65 mmol) was added and stirring was continued for one additional hour to ensure complete conversion of the Fmoc-Glu-OtBu starting material, as was confirmed by HPLC-MS analysis (program 2). Volatiles were removed in vacuo and the residue was taken up in EtOAc (50 mL) and washed with 1N KHSO$_4$ (3×50 mL) and Brine (3×50 mL) and dried (Na$_2$SO$_4$). The product was isolated by flash column chromatography (eluent: Et$_2$O) as a white foam (560 mg, 58%). R$_f$: 0.2 (eluent: Et$_2$O), R$_t$: 3.70 min (method 2), MS ES+ (amu) calculated: 582.24 [M]. found: 583.34 [M+H]$^+$, 605.33 [M+Na]$^+$, 527.2242 [(M−tBu)+H]$^+$; $^1$H NMR (300 MHz, CDCl$_3$) δ 9.19 (1H, s), 8.51 (1H, d, J=8.1 Hz), 7.73 (3H, m), 7.59 (2H, m), 7.49 (1H, J=8.7 Hz), 7.37 (2H, m), 7.27 (2H, m), 6.17 (1H, s), 5.87 (1H, d, J=8.1 Hz), 4.47 (1H, m), 4.40 (2H, m), 4.18 (1H, t, J=6.2 Hz), 2.52 (2H, m), 2.38 (3H, m), 2.04 (1H, m), 1.49 (9H, br s); $^{13}$C NMR (100 MHz, CDCl$_3$) δ 171.3, 171.0, 161.7, 156.8, 154.0, 153.0, 143.7 (double line), 142.3, 141.3, 127.7 (double line), 127.1 (double line), 125.3, 125.1, 125.0, 120.0 (double line), 115.8 (double line), 112.9, 106.7, 82.8, 67.1, 54.0, 47.2, 34.0, 29.4, 28.0, 18.5.

Alternative procedure for the synthesis of 2 using POCl$_3$:

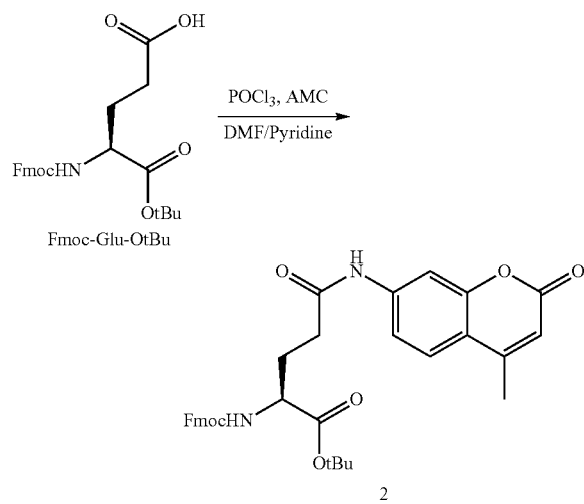

Fmoc-Glu(AMC)-OtBu (2). Under Nitrogen, POCl$_3$ (504 µL, 5.4 mmol) was added dropwise to a cooled (−15° C.) and stirred mixture of AMC (0.87 g, 4.9 mmol) and Fmoc-Glu(AMC)-OtBu (2.0 g, 4.7 mmol) in dry DMF/Pyridine (2:1 v/v, 100 mL). The reaction mixture was allowed to warm up to room temperature and stirring was continued for 16 h before the solvents were removed in vacuo. The residue was coevaporated with toluene and taken up in EtOAc (300 mL), washed with 1N KHSO$_4$ (2×200 mL) and Brine (2×200 mL) and dried (Na$_2$SO$_4$). The product was isolated by flash column chromatography (eluent: Et$_2$O) as a white foam (600 mg, 21%).

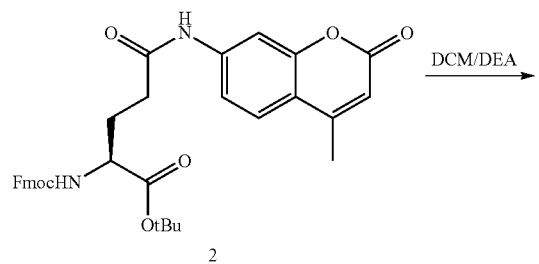

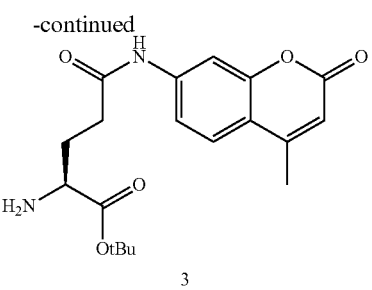

H-Glu(AMC)-OtBu (3). A portion of 2 (200 mg 0.34 mmol) was dissolved in diethylamine/dichloromethane (1:1 v/v, 16 mL) and stirred at room temperature. After 3 h the reaction mixture was concentrated in vacuo. The product was isolated by flash column chromatography (eluent: DCM→5% MeOH in DCM) as a white solid (92 mg, 75%). R. 0.2 (5% MeOH in DCM); R$_t$=2.22 min (method 2), MS ES+ (amu) calculated: 360.17 [M]; found 360.05 [M+H]$^+$, 305.05 [(M−tBu)+H]$^+$; $^1$H-NMR (300 MHz, DMSO-d$_6$) δ 10.38 (s, 1H), 7.76 (1H, d, J=2.0 Hz), 7.70 (1H d, J=8.7 Hz), 7.47 (1H dd, J=2.0, 8.7 Hz), 6.25 (1H, d, J=1.2 Hz), 3.23 (1H, m), 2.48 (2H, m, partially under DMSO peak), 2.40 (3H, s), 1.91 (1H, m), 1.80 (2H, m), 1.69 (1H, m), 1.40 (9H, s); $^{13}$C NMR (100 MHz, DMSO-d$_6$) 174.9, 171.7, 160.0, 153.7, 153.1, 142.6, 125.8, 115.0, 114.7, 112.1, 105.4, 79.9, 54.0, 32.8, 29.7, 27.7, 17.9.

Synthesis of and Characterization Compounds 1a-c and Ub-AMC General Method for the C-Terminal Modification of PupΔQ (1)

The PupΔQ sequence was synthesized on a trityl resin following the general procedure. Then, the resin bound polypeptide was treated with 5 mL of DCM/HFIP (7:3 v/v) for 30 min and filtered. This DCM/HFIP treatment was repeated once more and the resin was rinsed with DCM (3×5 mL). The combined filtrates were concentrated, coevaporated with DCM and dried under high vacuum. The partially protected peptide residue (1 equiv) was redissolved in DCM and reacted with H-Glu(AMC)-OtBu (45 mg, 125 µmol, 5 equiv) in the presence of PyBOP (65 mg, 125 µmol, 5 equiv) and TEA (35 µL, 250 µmol, 10 equiv). The reaction mixture was stirred over night at room temperature. The volatiles were removed in vacuo and the residue was treated with TFA/H$_2$O/TiS (95:2.5:2.5 v/v/v) for 3 h followed by precipitation with cold Et$_2$O/pentane (3:1 v/v). The precipitated crude protein was washed with Et$_2$O/pentane (3:1 v/v, once) and Et$_2$O (twice). Finally, the pellet was dissolved in a mixture of H$_2$O/CH$_3$CN/HOAc (65/25/10 v/v/v) and lyophilized. The crude product was purified by preparative HPLC.

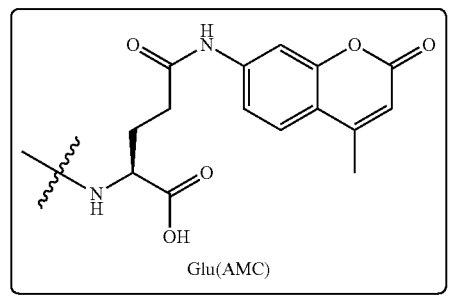 [SMILES: *N[C@@H](CCC(=O)Nc1ccc2c(C)cc(=O)oc2c1)C(=O)O]

Glu(AMC)

MAQEQTKRGGGGGDDDDIAGSTAAGQER-
REKLTEETDDLLDEIDDVLE ENAEDFVRAYVQKGG-

Glu(AMC) (1a; SEQ ID NO: 5). Yield: 4.3 mg (4%), $R_t$: 7.08 min (method 1), MS ES+ (amu) calculated: 7098 [M]. found 7099 [M+H]+.

EETDDLLDEIDDVLEENAEDFVRAYVQKGG-Glu (AMC) (1b; SEQ ID NO: 6). Yield: 2.1 mg (5%), $R_t$: 7.78 min (method 1), MS ES+ (amu) calculated: 3711 [M]. found 3711 [M+H]+.

DDVLEENAEDFVRAYVQKGG-Glu(AMC) (1c; SEQ ID NO: 7). Yield: 4.3 mg (4%), $R_t$: 6.62 min (method 1), MS ES+ (amu) calculated: 2538 [M]. found 2539 [M+H]+.

Ub-AMC. The synthesis of ubiquitin-AMC was performed following the procedure as was described earlier (El Oualid et al *Angew. Chem. Int. Ed.*, 2010, 49, 10149-10153).

An alternative way of making PupAMC or Pup equipped with other reported groups as mentioned above or N-terminally truncated derivatives makes use of intein chemistry. Pup(1-63) or a desired N-terminal truncation is then expressed as an intein fusion protein similar to the methods described in Borodovsky et al. Chem Biol. 2002 October; 9(10):1149-59, the content of which is incorporated herein in its entirety. In this method intein technology is used to generate the desired Pup(1-63) thioester or an N-terminally truncated derivative. The thus obtained thioester is then reacted with the desired glutamic acid derivative such as GluAMC depicted above according to procedures in the above mentioned reference.

Additional methods of making modified Pup, including Pup-luciferin (a luminogenic moiety) and Pup modified with a fluorescent moiety such that it is assayable using Fluorescence Polarization (FP), are described in, for example, WO 2010/131962, the entire content of which is incorporated herein by reference in its entirety.

Dop Activity Assays

Photometric Assays

Reactions contained Dop-His$_6$ (3 µg),[4a] substrate (2 µM), ATP (2.5 mM), MgCl$_2$ (20 mM), DTT (1 mM), and NaCl (50 mM) in Tris (50 mM, pH8) in a final volume of 100 µL in a 96-well plate format. Reactions were monitored by measuring the increase in fluorescence emission at 460 nm ($\lambda$ex=355 nm) that correlates with hydrolysis of AMC from the substrate on a SpectraMax M5 (Molecular Devices) spectrophotometer. SoftMax Pro (Molecular Devices) was used to measure the data and GraphPad Prism was used to fit the kinetic data.

For Mtb lysate experiments, Mtb were grown to an $OD_{580}$=1-1.2 after which 50 OD equivalents were harvested, washed with 25 mL of 0.05% Tween-80 in PBS. The cells were resuspended in Tris (1 mL, 100 mM, pH8, EDTA (1 mM) and transferred to bead beating tubes with zirconia silica beads (250 µL). Cells were lysed by bead beating three times for 30 sec each time. Lysates were filtered through 0.45 µm filters, glycerol was added to 12% final volume and the samples were either analyzed immediately or stored at −20° C. for further use. Lysate reactions contained lysate (40 µL), substrate 1a (3 µM), ATP (5 mM), MgCl$_2$ (20 mM), DTT (1 mM), 1× energy regeneration solution (Boston Biochem) and NaCl (50 mM) in Tris (50 mM, pH8) in a final volume of 100 µL.

Mass Spectrometric Assays

To a solution of peptide 1a, 1b, 1c or Ub-AMC (3.3 µM) in assay buffer (containing: ATP (2.5 mM), MgCl$_2$ (20 mM), DTT (1 mM), and NaCl (50 mM) in Tris (50 mM, pH8)), Dop-His$_6$[4a] was added and the mixture was incubated at RT for 2 h. As a control, a solution of the peptide (3.3 µM) in assay buffer without added Dop-His$_6$ was incubated at RT for 2 h. After 2 h, CH$_3$CN (60 µL) was added to both reaction vials, the samples were centrifuged at 13.000 rpm for 5 min. Aliquots (25 µL) were taken from each mixture for ESMS analysis.

Compounds/agents (e.g., small molecules) identified through screening methodologies utilizing cell-free assay systems can be further tested in cell-based assays and in vivo assays.

In accordance with this embodiment, cells expressing endogenous or recombinant Pup or a functional fragment thereof, are contacted with the candidate compound identified in a cell-free assay as described above or a control compound and the ability of the candidate compound to modulate Pup activity in cells is determined. The cell, for example, can be of prokaryotic origin (e.g., *E. coli*) and in a particular embodiment is a prokaryotic cell that expresses endogenous Dop or is engineered to express Dop.

In another embodiment, candidate compounds identified in cell-free assays are evaluated in an animal model wherein their ability to modulate Pup activity can be assessed in the context of, for example, an Mtb infection. Examples of suitable animals include, but are not limited to, mice, rats, rabbits, monkeys, guinea pigs, dogs and cats. Preferably, the animal used represents a model of a disease caused by a bacterial infection (e.g., tuberculosis). In accordance with this embodiment, the test compound or a control compound is administered (e.g., by inhalation, orally, rectally or parenterally such as intraperitoneally or intravenously) to a suitable animal and the effect on the level of activity is determined.

In a further embodiment of the invention, candidate compounds able to modulate Pup in at least one of the above screening assays are modified by methods known in the art to further improve specific characteristics, e.g., to increase efficacy and/or specificity and/or solubility. Selected compounds exhibiting the most desired characteristics are designated lead compounds, and further tested in, for example, animal models of tuberculosis (such as, e.g., mice) to measure their efficacy.

The basic molecular biology techniques used to practice the methods of the invention are well known in the art, and are described for example in Sambrook et al., 1989, *Molecular Cloning: A Laboratory Manual*, Cold Spring Harbor Laboratory, New York; Ausubel et al., 1988, *Current Protocols in Molecular Biology*, John Wiley & Sons, New York; and Ausubel et al., 2002, *Short Protocols in Molecular Biology*, John Wiley & Sons, New York).

Therapeutic Uses of Agents Able to Bind and/or Modulate Pup Activity and Pupylation The invention provides for treatment of a disease caused by a bacterial infection (e.g., tuberculosis) by administration of a therapeutic compound identified using the above-described methods. Such compounds include, but are not limited to proteins, peptides, protein or peptide derivatives or analogs, antibodies, nucleic acids, and small molecules.

The invention provides methods for treating patients afflicted with a bacterial infection (e.g., tuberculosis) comprising administering to a subject an effective amount of a compound identified by the method of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human. In a specific embodiment, a non-human mammal is the subject.

Formulations and methods of administration that can be employed when the compound comprises a nucleic acid are described above; additional appropriate formulations and routes of administration are described below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu (1987) J. Biol. Chem. 262:4429-4432), and construction of a nucleic acid as part of a retroviral or other vector. Methods of introduction can be enteral or parenteral and include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally, e.g., by local infusion during surgery, topical application, e.g., by injection, by means of a catheter, or by means of an implant, said implant being of a porous, non-porous, or gelatinous material, including membranes, such as sialastic membranes, or fibers.

In another embodiment, the compound can be delivered in a vesicle, in particular a liposome (see Langer (1990) Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound can be delivered in a controlled release system. In one embodiment, a pump may be used (see Langer, supra; Sefton (1987) CRC Crit. Ref. Biomed. Eng. 14:201; Buchwald et al. (1980) Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., 1983, Macromol. Sci. Rev. Macromol. Chem. 23:61; see also Levy et al. (1985) Science 228:190; During et al. (1989) Ann. Neurol. 25:351; Howard et al. (1989) J. Neurosurg. 71:105). In yet another embodiment, a controlled release system can be placed in proximity of the therapeutic target, i.e., a target tissue or tumor, thus requiring only a fraction of the systemic dose (see, e.g., Goodson, in Medical Applications of Controlled Release, supra, vol. 2, pp. 115-138 (1984)). Other controlled release systems are discussed in the review by Langer (1990, Science 249:1527-1533).

Pharmaceutical Compositions

The present invention also provides pharmaceutical compositions. Such compositions comprise a therapeutically effective amount of an agent, and a pharmaceutically acceptable carrier. In a particular embodiment, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E.W. Martin, incorporated in its entirety by reference herein. Such compositions will contain a therapeutically effective amount of the compound, preferably in purified form, together with a suitable amount of carrier so as to provide the form for proper administration to the subject. The formulation should suit the mode of administration.

In a particular embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment of a disease caused by a bacterial infection (e.g., tuberculosis) can be determined by standard clinical techniques based on the present description. In addition, in vitro assays may optionally be employed to help identify optimal dosage ranges. The precise dose to be employed in the formulation will also depend on the route of administration, and the seriousness of the disease, and should be decided according to the judgment of the practitioner and each subject's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Suppositories generally contain active ingredient in the range of 0.5% to 10% by weight; oral formulations preferably contain 10% to 95% active ingredient. Effective doses may be extrapolated from dose-response curves derived from in vitro or animal model test systems.

Nucleic Acids

The invention provides methods of identifying agents capable of binding and/or modulating Pup. Accordingly, the invention encompasses administration of a nucleic acid encoding a peptide or protein capable of modulating an activity of Pup, as well as antisense sequences or catalytic RNAs capable of interfering with the expression and/or activity of Pup.

In one embodiment, a nucleic acid comprising a sequence encoding a peptide or protein capable of competitively binding to Pup is administered. Any suitable methods for administering a nucleic acid sequence available in the art can be used according to the present invention.

Methods for administering and expressing a nucleic acid sequence are generally known in the area of gene therapy. For general reviews of the methods of gene therapy, see Goldspiel et al. (1993) Clinical Pharmacy 12:488-505; Wu and Wu (1991) Biotherapy 3:87-95; Tolstoshev (1993) Ann. Rev. Pharmacol. Toxicol. 32:573-596; Mulligan (1993) Science 260:926-932; and Morgan and Anderson (1993) Ann. Rev. Biochem. 62:191-217; May (1993) TIBTECH 11(5): 155-215. Methods commonly known in the art of recombinant DNA technology which can be used in the present invention are described in Ausubel et al. (eds.), 1993, Current Protocols in Molecular Biology, John Wiley & Sons, NY; and Kriegler (1990) Gene Transfer and Expression, A Laboratory Manual, Stockton Press, NY.

In a particular aspect, the compound comprises a nucleic acid encoding a peptide or protein capable of binding to and/or modulating an activity of Pup (such as the ability to be conjugated to a proteasome substrate or be recognized by a enzyme involved in pupylation or de-pupylation of a substrate), such nucleic acid being part of an expression vector that expresses the peptide or protein in a suitable host. In particular, such a nucleic acid has a promoter operably linked to the coding region, said promoter being inducible or constitutive (and, optionally, tissue-specific). In another particular embodiment, a nucleic acid molecule is used in which the coding sequences and any other desired sequences are flanked by regions that promote homologous recombination at a desired site in the genome, thus providing for intrachromosomal expression of the nucleic acid (Koller and Smithies (1989) Proc. Natl. Acad. Sci. USA 86:8932-8935; Zijlstra et al. (1989) Nature 342:435-438).

Delivery of the nucleic acid into a subject may be direct, in which case the subject is directly exposed to the nucleic acid or nucleic acid-carrying vector; this approach is known as in vivo gene therapy. Alternatively, delivery of the nucleic acid into the subject may be indirect, in which case cells are first transformed with the nucleic acid in vitro and then transplanted into the subject, known as "ex vivo gene therapy".

In another embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286); by direct injection of naked DNA; by use of microparticle bombardment (e.g., a gene gun; Biolistic, Dupont); by coating with lipids, cell-surface receptors or transfecting agents; by encapsulation in liposomes, microparticles or microcapsules; by administering it in linkage to a peptide which is known to enter the nucleus; or by administering it in linkage to a ligand subject to receptor-mediated endocytosis (see, e.g., Wu and Wu, 1987, J. Biol. Chem. 262:4429-4432), which can be used to target cell types specifically expressing the receptors.

In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932-8935; Zijlstra et al. (1989) Nature 342:435-438).

In a further embodiment, a retroviral vector can be used (see Miller et al. (1993) Meth. Enzymol. 217:581-599). These retroviral vectors have been modified to delete retroviral sequences that are not necessary for packaging of the viral genome and integration into host cell DNA. The nucleic acid encoding a desired polypeptide to be used in gene therapy is cloned into the vector, which facilitates delivery of the gene into a subject. More detail about retroviral vectors can be found in Boesen et al. (1994) Biotherapy 6:291-302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al. (1994) J. Clin. Invest. 93:644-651; Kiem et al. (1994) Blood 83:1467-1473; Salmons and Gunzberg (1993) Human Gene Therapy 4:129-141; and Grossman and Wilson (1993) Curr. Opin. in Genetics and Devel. 3:110-114.

Adenoviruses may also be used effectively in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson (1993) Current Opinion in Genetics and Development 3:499-503 present a review of adenovirus-based gene therapy. Bout et al. (1994) Human Gene Therapy 5:3-10 demonstrated the use of adenovirus vectors to transfer genes to the respiratory epithelia of rhesus monkeys. Other instances of the use of adenoviruses in gene therapy can be found in Rosenfeld et al. (1991) Science 252:431-434; Rosenfeld et al. (1992) Cell 68:143-155; Mastrangeli et al. (1993) J. Clin. Invest. 91:225-234; PCT Publication WO94/12649; and Wang, et al. (1995) Gene Therapy 2:775-783. Adeno-associated virus (AAV) has also been proposed for use in gene therapy (Walsh et al. (1993) Proc. Soc. Exp. Biol. Med. 204:289-300; U.S. Pat. No. 5,436,146).

Another suitable approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr (1993) Meth. Enzymol. 217:599-618; Cohen et al. (1993) Meth. Enzymol. 217:618-644; Cline (1985) Pharmac. Ther. 29:69-92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a subject by various methods known in the art. In a preferred embodiment, epithelial cells are injected, e.g., subcutaneously. In another embodiment, recombinant skin cells may be applied as a skin graft onto the subject; recombinant blood cells (e.g., hematopoietic stem or progenitor cells) are preferably administered intravenously. The amount of cells envisioned for use depends on the desired effect, the condition of the subject, etc., and can be determined by one skilled in the art.

Cells into which a nucleic acid can be introduced for purposes of gene therapy encompass any desired, available cell type, and include but are not limited to neuronal cells, glial cells (e.g., oligodendrocytes or astrocytes), epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood or fetal liver. In a preferred embodiment, the cell used for gene therapy is autologous to the subject that is treated.

In another embodiment, the nucleic acid to be introduced for purposes of gene therapy may comprise an inducible promoter operably linked to the coding region, such that expression of the nucleic acid is controllable by adjusting the concentration of an appropriate inducer of transcription.

Direct injection of a DNA coding for a peptide or protein capable of binding to and/or modulating an activity of Pup may also be performed according to, for example, the techniques described in U.S. Pat. No. 5,589,466. These techniques involve the injection of "naked DNA", i.e., isolated DNA molecules in the absence of liposomes, cells, or any other material besides a suitable carrier. The injection of DNA encoding a protein and operably linked to a suitable promoter results in the production of the protein in cells near the site of injection.

Kits

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and described the methods and/or materials in connection with which the publications are cited.

EXAMPLE I

Methods and Materials
Synthesis of Peptides 1a-c

The PupΔQ sequence was synthesized on a pre-loaded Fmoc amino acid trityl resin (0.2 mmol/g) at 25 μmol scale, using fourfold excess of appropriately side chain protected Fmoc-amino acids in NMP relative to the resin, PyBOP (4 equiv) and DIPEA (8 equiv) were used as condensing reagents. Fmoc removal was carried out using 20% piperidine in NMP for 2×2 and 1×5 min and capping of the resin was performed with a mixture of Ac$_2$O/DIPEA/HOBt in NMP at 500 mM, 125 mM and 15 mM respectively (3×1.2 mL, 2×2 and 1×5 min). During the synthesis different coupling protocols were used; coupling cycle 1-30: single couplings of 40 min, double couplings of 2×40 min for cycles 21, 22, 24 and 28, no capping; coupling cycle 31-39: single couplings of 60 min, double couplings of 2×60 min for cycles 33, 34, 38 and 39, no capping; coupling cycle 40-61: single couplings of 60 min, double couplings of 2×60 min for cycles 40, 42, 46, 48, 51-54, 58 and 59, capping after each coupling cycle. During the chain elongation, dipeptide pseudoproline building blocks were incorporated at positions 21/22 (Fmoc-Ser-Thr($\Psi^{Me,Me}$pro)-OH) and 32/33 (Fmoc-Leu-Thr($\Psi^{Me,Me}$pro)-OH. After completion of the solid phase peptide synthesis, the resin was washed with Et$_2$O, dried under high vacuum and stored for further use.

Then, the resin bound polypeptide was treated with 5 mL of DCM/HFIP (7:3 v/v) for 30 min and filtered. This DCM/HFIP treatment was repeated once more and the resin was rinsed with DCM (3×5 mL). The combined filtrates were concentrated, coevaporated with DCM and dried under high vacuum. The partially protected peptide residue (1 equiv) was redissolved in DCM and reacted with H-Glu(AMC)-OtBu (45 mg, 125 μmol, 5 equiv) in the presence of PyBOP (65 mg, 125 μmol, 5 equiv) and TEA (35 μL, 250 μmol, 10 equiv). The reaction mixture was stirred over night at room temperature. The volatiles were removed in vacuo and the residue was treated with TFA/H$_2$O/TiS (95:2.5:2.5 v/v/v) for 3 h followed by precipitation with cold Et$_2$O/pentane (3:1 v/v). The precipitated crude protein was washed with Et$_2$O/pentane (3:1 v/v, once) and Et$_2$O (twice). Finally, the pellet was dissolved in a mixture of H$_2$O/CH$_3$CN/HOAc (65/25/10 v/v/v) and lyophilized. The crude product was purified by preparative HPLC on a Waters Atlantis prep T3™ (10×150 mm, 5 μm) column, using 2 mobile phases: A=0.1% TFA in water and B=0.1% formic acid in CH$_3$CN with the following gradient: 0-5 min: 5% B; 5-8 min:→25% B; 8-30 min:→60% B; 30-33 min:→95% B; 33-35 min: 95% B.

MAQEQTKRGGGGGDDDDIAGSTAAGQER-REKLTEETDDLLDEIDDV LEENAEDFVRAYVQKGG-Glu(AMC) (1a; SEQ ID NO: 5). Yield: 4.3 mg (4%), R$_t$: 7.08 min (analytical HPLC-MS was performed on a Waters Alltima C18 (2.1×100 mm, 3 μM) column using 2 mobile phases: A=0.1% formic acid in water and B=0.1% formic acid in CH₃CN under the following conditions: flow rate=0.4 mL/min, runtime=20 min, column T=40° C. Gradient: 0-1 min: 5% B; 1-11 min:→95% B; 11-16 min: 95% B), MS ES+ (amu) calculated: 7098 [M]. found 7099 [M+H]$^+$.

EETDDLLDEIDDVLEENAEDFVRAYVQKGG-Glu (AMC) (1b; SEQ ID NO: 6). Yield: 2.1 mg (5%), $R_t$: 7.78 min (analytical HPLC-MS was performed in the same fashion as for 1a), MS ES+ (amu) calculated: 3711 [M]. found 3711 [M+H]$^+$.

DDVLEENAEDFVRAYVQKGG-Glu(AMC) (1c; SEQ ID NO: 7). Yield: 4.3 mg (4%), $R_t$: 6.62 min (analytical HPLC-MS was performed in the same fashion as for 1a), MS ES+ (amu) calculated: 2538 [M]. found 2539 [M+H]$^+$.

H-Glu(AMC)-OtBu: Synthetic details on the preparation of H-Glu(AMC)-OtBu and characterization data are included herein above.

Photometric Assays

Reactions contained Dop-His$_6$ (3 μg),$^{4a}$ substrate (2 μM), ATP (2.5 mM), MgCl$_2$ (20 mM), DTT (1 mM), and NaCl (50 mM) in Tris (50 mM, pH8) in a final volume of 100 μL in a 96-well plate format. Reactions were monitored by measuring the increase in fluorescence emission at 460 nm (λex=355 nm) that correlates with hydrolysis of AMC from the substrate on a SpectraMax M5 (Molecular Devices) spectrophotometer. SoftMax Pro (Molecular Devices) was used to measure the data and GraphPad Prism was used to fit the kinetic data.

For Mtb lysate experiments, Mtb were grown to an OD$_{580}$=1-1.2 after which 50 OD equivalents were harvested, washed with 25 mL of 0.05% Tween-80 in PBS. The cells were resuspended in Tris (1 mL, 100 mM, pH8, EDTA (1 mM) and transferred to bead beating tubes with zirconia silica beads (250 μL). Cells were lysed by bead beating three times for 30 sec each time. Lysates were filtered through 0.45 μm filters, glycerol was added to 12% final volume and the samples were either analyzed immediately or stored at −20° C. for further use. Lysate reactions contained lysate (40 μL), substrate 1a (3 μM), ATP (5 mM), MgCl$_2$ (20 mM), DTT (1 mM), 1× energy regeneration solution (Boston Biochem) and NaCl (50 mM) in Tris (50 mM, pH8) in a final volume of 100 μL.

Mass Spectrometric Assays

To a solution of peptide 1a, 1b, 1c or Ub-AMC (3.3 μM) in assay buffer (containing: ATP (2.5 mM), MgCl$_2$ (20 mM), DTT (1 mM), and NaCl (50 mM) in Tris (50 mM, pH8)), Dop-His$_6$$^{4a}$ was added and the mixture was incubated at RT for 2 h. As a control, a solution of the peptide (3.3 μM) in assay buffer without added Dop-His$_6$ was incubated at RT for 2 h. After 2 h, CH₃CN (60 μL) was added to both reaction vials, the samples were centrifuged at 13.000 rpm for 5 min. Aliquots (25 μL) were taken from each mixture for ESMS analysis.

Results

To develop the reagents required for performing screening assays to identify agents/compounds capable of modulating (e.g., inhibiting) Pup and PPS, the present inventors envisaged a Dop assay reagent that is based on Pup, its natural substrate, and a reporter group that becomes fluorescent after cleavage from Pup. Introduction of the fluorophore AMC (amino methyl coumarin) to the side chain of the C-terminal glutamate of Pup would make possible measurement of Dop activity by monitoring the increase in fluorescence over time, representing the hydrolysis of the AMC moiety from Pup. A similar reagent, Ub-AMC, has been used extensively to monitor deubiquitinase activity (Dang et al., *Biochemistry* 1998, 37, 1868-1879).

In principle the relatively small size of Pup and its inherently disordered structure make it amenable to chemical peptide synthesis. However, synthesis of such a reagent is extremely challenging. Pup consists of 64 amino acids and the introduction of AMC through condensation with carboxylic acids often proceeds sluggishly. The present inventors have reported a high-yielding Fmoc-based linear solid-phase peptide synthesis (SPPS) of Ub reagents that allows for the incorporation of tags and mutations as well as specific C-terminal modifications in a straightforward manner (El Oualid et al., *Angew Chem Int Ed Engl* 2010, 49 (52), 10149-10153; the entire content of which is incorporated herein in its entirety). Using similar, but distinct, Fmoc SPPS protocols, including the incorporation of dipeptide pseudoproline building blocks at positions 21/22 (Fmoc-Ser-Thr(Ψ$^{Me,Me}$pro)-OH) and 32/33 (Fmoc-Leu-Thr(Ψ$^{Me,Me}$pro)-OH), the present inventors synthesized the Pup(1-63) sequence (lacking the C-terminal Glu residue) as was confirmed by HPLC-MS analysis. Omission of the dipeptide building blocks led to a less productive synthesis. The polypeptide was built up on a hyper-acid-labile trityl resin which allows mild detachment from the resin with 30% HFIP/DCM to afford protected Pup(1-63) with a free C-terminal carboxylate available for coupling with an AMC-labelled glutamine analogue (FIG. 2; Scheme 2). Therefore a suitably protected building block was synthesized starting from commercial Fmoc-Glu-OtBu and AMC. The synthesis of coumarides is difficult because of the poor nucleophilicity of the aniline amino group and traditional peptide coupling methods using EDC/DMAP failed. However, when phosphoryl chloride was used for carboxyl activation, the Fmoc-Glu (AMC)-OtBu product could be obtained, albeit in low yield of 21% (Rijkers et al., *Rect. Tray. Chim. Pays-Bas* 1991, 110, 347-348). Gratifyingly, formation of the acid chloride in situ under neutral conditions using Ghosez's reagent (Haveaux et al., *Organic Syntheses* 1979, 59, 26), an α-chloroenamine, followed by the addition of AMC, led to a satisfying yield of 56%. The Fmoc protecting group was removed with 50% diethylamine in DCM and the resulting H-Glu(AMC)-OH building block was reacted with protected Pup(1-63) in the presence of PyBOP and DIPEA as the condensing reagents. After deprotection and purification, the Pup-Glu(AMC) conjugate was obtained with high purity and 4% overall yield (based on initial resin loading).

Since smaller reagents are synthetically more accessible, the present inventors sought to generate modified functional fragments of Pup. Further to this point, it has previously been shown that the amino-terminus of Pup is not essential for Dop activity (Burns et al., *J Bacteriol* 2010, 192 (11), 2933-2935; Sutter et al., *FEBS Letters* 2009, 583, 3151-3157). In that Pup, however, is an intrinsically disordered protein (IDP), functional motifs are not readily recognizable therein and thus, there was no way to predict which fragments thereof would be functional fragments with respect to acting as Dop substrates. Accordingly, the present inventors synthesized truncated Pup-Glu(AMC) analogues which included fragments of Pup that were chosen arbitrarily. The first two truncated Pup-Glu (AMC) analogues synthesized contain 30 amino acid (Pup (33-63)-Glu(AMC), 1b) and 20 amino acid (Pup(43-63)-Glu (AMC), 1c) long sequences, respectively, that have a GluAMC residue attached to their C-termini, and which were evaluated for comparison purposes to full length Pup(1-63)-Glu(AMC) (1a) in Dop assays (FIG. 2; Scheme 2). All Pup-Glu(AMC) analogues were obtained in high purity and in similar overall yields. Each construct was tested as a substrate for Dop by monitoring the increase in fluorescence over time, representing cleavage of AMC from the C-terminal glutamine side chain of the Pup analogue. To confirm that the observed fluorescence originated from AMC cleavage, all reaction mixtures were also analyzed by mass spectrometry.

Figure 3:
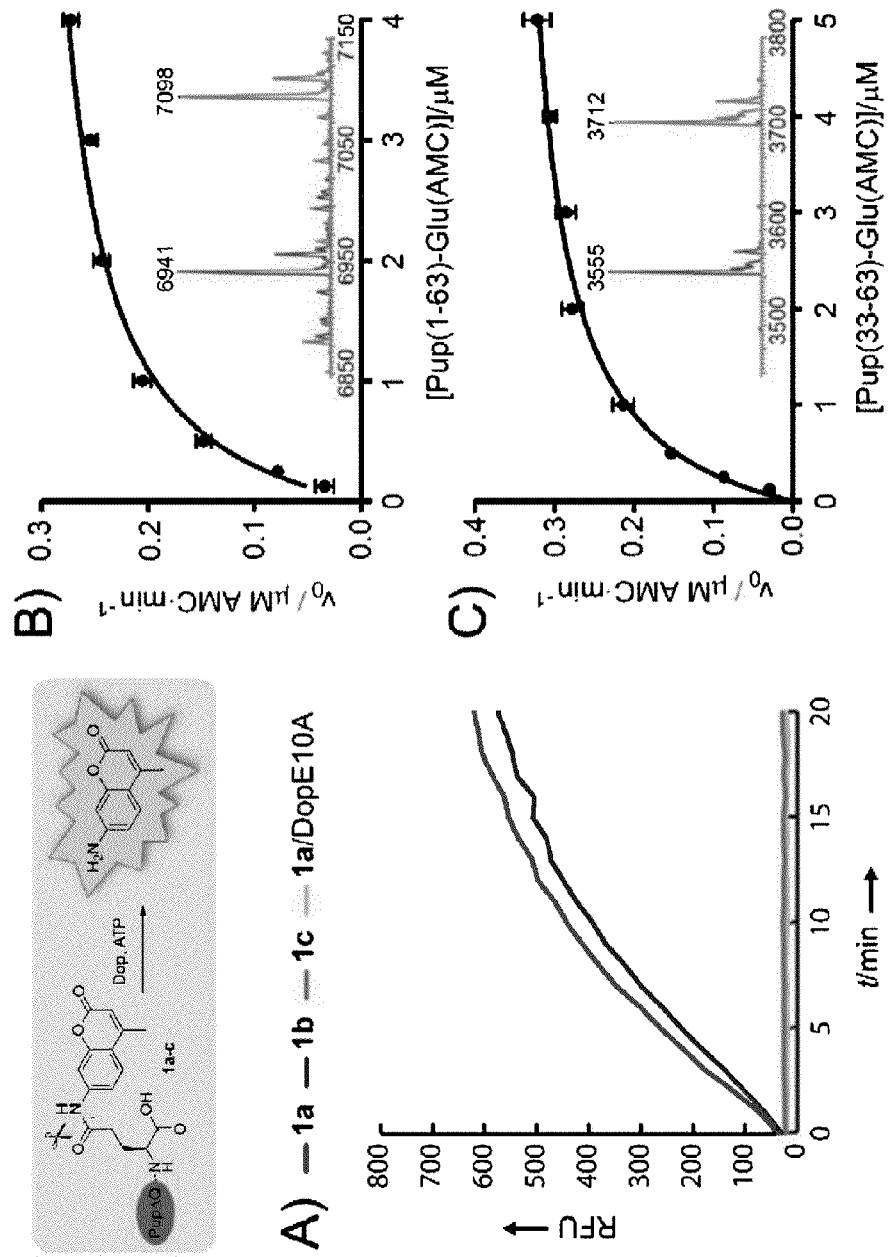
FIG. 3A-C shows Dop activity assays. A) Analysis of Dop activity with Pup-Glu(AMC) conjugates 1a-c, assays were performed by following the release of free coumarin (AMC)

Dop showed hydrolytic activity for both Pup(1-63)-Glu (AMC) (1a) and Pup(33-63)-Glu(AMC) (1b) however, Pup (43-63)-Glu(AMC) (1c) was not a substrate for Dop (FIG. 3). These results support the previous findings that the amino-terminus of Pup is disposable for Dop activity, and also suggest that the Dop binding region extends beyond the C-terminus of Pup, into the middle of the protein. This is a surprising finding in view of the fact that this region is important for making critical contacts with Mpa, the proteasomal ATPase (Wang et al Nat Str Mol Biol 2010), and thus, is implicated in degradation pathways, but is not known to be recognized by Dop.

The Dop substrates Pup(1-63)-Glu(AMC) (1a) and Pup (33-63)-Glu(AMC) (1b) were subjected to further analyses and their kinetic constants were determined (FIG. 3b,c and Table 1). The data followed typical Michaelis-Menten kinetics and the $K_m$ values were comparable with one another along with various deubiquitinating enzymes (UCH-L3=0.039 µM; IsoT=1.4 µM, determined using Ub-AMC as substrate; Dang et al., *Biochemistry* 1998, 37, 1868-1879). Despite a relatively low $K_m$, the $k_{cat}$ for Dop was found to be rather low as well. Its value compares to that of the Pup ligase PafA ($K_m$=1.4 µM; $k_{cat}$=0.95 min$^{-1}$, determined using PupGGE as a substrate; Guth et al., *J Biol Chem* 2011, 286 (6), 4412-4419). It is possible that the kinetics of the reaction were affected by the artificial nature of the substrate, i.e. AMC is a bulky hydrophobic group in comparison to the lysine side chain of a natural substrate. Interestingly, Imkamp and colleagues observed that Dop activity increased in the presence of the ATPase Mpa, which might interact with Pup, or Pup and Dop, to increase $k_{cat}$ values in vivo (Imkamp et al., *EMBO Rep* 2010, 11 (10), 791-797). DopE10A the mutant proposed to be deficient in ATP binding, showed no activity with Pup (1-63)-Glu(AMC). Also, Dop was unable to hydrolyze Ub-AMC, the substrate for deubiquitinases.

TABLE 1

Dop kinetics obtained with different synthetic substrates

| Substrate | kcat (min$^{-1}$) | Km (µM) | kcat/Km (MS$^{-1}$) |
|---|---|---|---|
| 1a | 0.60 ± 0.02 | 0.65 ± 0.07 | 15384 |
| 1b | 0.68 ± 0.02 | 0.75 ± 0.08 | 15111 |
| 1c | n.a. | n.a. | n.a. |
| 1a/DopE10A | n.a. | n.a. | n.a. |
| Ub-AMC | n.a. | n.a. | n.a. |

(n.a. = no activity)

To investigate the specificity of our synthetic Dop substrates, the present inventors monitored the hydrolysis of Pup(1-63)-Glu(AMC) (1a) in lysates of Mtb as well as lysates of *E. coli* (FIG. 4). Notably, lysates from wild type (WT) Mtb, PafA deficient mutant Mtb, and complemented Dop deficient mutant Mtb showed Pup(1-63)-Glu(AMC) (1a) hydrolysis, whereas Dop deficient mutant Mtb, Dop deficient mutant Mtb complemented with the ATP-binding defective mutant DopE10A and *E. coli* could not hydrolyze Pup(1-63)-Glu (AMC) (1a) under the conditions used. These results illustrate the high specificity of Pup(1-63)-Glu(AMC) (1a) for Dop, even in lysates.

In summary, the present inventors have developed new Pup-based fluorogenic substrates with high specificity towards hydrolysis by Dop, even in an Mtb lysate. Moreover, Pup(33-63)-Glu(AMC) (1b), an amino-terminal truncated analog of Pup, performed equally well as the full length Pup-Glu(AMC) conjugate. The shorter Pup(43-63)-Glu (AMC) (1c) conjugate, however, did not prove to be a Dop substrate. Since Dop is as an attractive new drug target for Mtb, the fluorogenic substrates described herein are promising reagents for high-throughput screening assays directed to the identification of Dop inhibitors. In view of the regulatory relationship of Dop and Pup, such inhibitors would, moreover, be Pup inhibitors as well as general PPS inhibitors.

EXAMPLE II

High Throughput Dop Inhibitor Screens

In the interests of developing second generation Dop substrates having structural/functional properties that differ from Pup-AMC conjugates, the present inventors have explored the utility of different fluorescent moieties and different lengths of Pup sequences. One of the structural/functional properties of Pup-AMC that the present inventors sought to modify is the detection of the AMC fluorophore (λEx/Em=450 nm/350 nm), which can be adversely affected by autofluorescence of cell lysate components and screening compounds. It is, of course, noteworthy that such complications can be avoided, at least in part, by using a totally purified system. In that many reliable screening results are obtained with assay reagents that best resemble the natural substrates, there was, however, motivation to generate a full length Pup (1-64) conjugate. Along these lines, and given that Pup(1-63)-Glu(AMC) lacks the "native" Lys-Glu isopeptide bond at the C-terminus, it was desirable to generate a full length Pup conjugate, at least for the purposes of confirmation of screening assays performed with Pup(1-63)-Glu(AMC) (1a).

Fluorescence Polarization (FP) is a convenient assay format in HTS. Advantages of FP over more conventional methods to study protein binding include a lower detection limit in the sub-nanomolar range and insensitivity to variations in substrate concentrations (Huang et al., *Methods in Molecular Biology*, 2009, 565, 127). FP measures the parallel and perpendicular components of fluorescence emission using plane polarized excitation. Polarization values (measured in mP units) for fluorophore-Pup conjugates are inversely related to the speed of their molecular rotation. During the assay, the fluorophore is cleaved from Pup. As the free fluorophore rotates faster, the polarization value will decrease. The magnitude of this change in polarization can be used to quantitatively measure Dop activity (FIG. 7A). TAMRA (5-Tetramethylrhodamine) is chosen as the fluorophore because it emits at a wavelength (λEx/Em=531 nm/579 nm) that is high enough to be free from most of the auto-fluorescence background of compounds in a diverse library of small molecules. The fluorophore is introduced into the Pup glutamyl side-chain carboxylate via the ε-amino moiety of a minimal TAMRA-lysine-glycine dipeptide sequence. In this way the Dop cleavage site features an isopeptide bond which resembles the natural Pup-protein linkage.

This FP screening reagent will be evaluated in a test screen for assay optimization. The LOPAC1280™ library, a collection of 1,280 pharmacologically active compounds which is available from the NKI screening facility has been selected for this purpose. In the assay, substrate turnover will be measured by the polarization value, which serves as a readout for enzyme activity. At the outset, recombinantly expressed Dop will be used. In subsequent test screens, Mycobacterial lysates will be used instead of purified Dop protein.

Once protocols have been established in the initial test screen, larger compound libraries will be screened.

The hits from the above in vitro screens will be validated in vivo. Such in vivo assays are described herein and include testing on intact bacteria, infected primary macrophages from mice and eventually in animal models under infectious conditions. For additional information on in vivo assays, see, e.g., Pearce et al., *The EMBO J.* 2006, 25 (22), 5423-5432; Pearce et al. 2008 Science 322:1104-1107; and Darwin et al. 2003 Science 302:1963-1966; the entire content of each of which is incorporated herein in its entirety.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A purified synthetic prokaryotic ubiquitin-like protein (Pup) comprising the amino acid sequence spanning positions 1-63 of Pup as set forth in SEQ ID NO: 2, wherein the carboxylate of amino acid glycine at position 63 of SEQ ID NO: 2 is attached via a covalent linkage to a modified glutamic acid (Glu), wherein the modified Glu is attached via the gamma-carboyxlate side chain of Glu to a synthetic fluorogenic or luminescent reporter moiety.

2. The purified synthetic Pup of claim 1, wherein the synthetic fluorogenic reporter moiety is amino methyl coumarin (AMC), 5-tetramethylrhodamine (TAMRA), quenched rhodamine, lys[(alpha tetramethylrhodamine (TMR)], or amino trifluoromethyl coumarin (AFC).

3. The synthetic purified synthetic Pup of claim 2, wherein the quenched rhodamine is rhodamine110.

4. A purified synthetic prokaryotic ubiquitin-like protein (Pup) comprising the amino acid sequence spanning positions 33-63 of Pup as set forth in SEQ ID NO: 2, wherein the carboxylate of amino acid glycine at position 63 of SEQ ID NO: 2 is attached via a covalent linkage to a modified glutamic acid (Glu), wherein the modified Glu is attached via the gamma-carboyxlate side chain of Glu to a synthetic fluorogenic or luminescent reporter moiety.

5. A method of making a synthetic Pup of claim 1 or claim 4 comprising a C-terminus modification, wherein the C-terminus modification is a fluorescent or a luminescent reporter moiety, the method comprising:
   a) providing a polypeptide comprising the amino acid sequence 1-63 of Pup as set forth in SEQ ID NO: 2 or a polypeptide comprising the amino acid sequence 33-63 of Pup as set forth in SEQ ID NO: 2, wherein the polypeptide comprises a free C-terminal carboxylate; and
   b) coupling the polypeptide comprising a free C-terminal carboxylate to H-(Glu(fluorescent or luminescent reporter moiety)—OH in the presence of condensing reagents to generate the synthetic Pup of claim 1 or claim 4.

6. The method of claim 5, wherein the fluorescent moiety is amino methyl coumarin (AMC) and the H-Glu(fluorescent moiety)—OH is H-Glu(AMC)—OH.

7. The method of claim 5, wherein the condensing reagents are PyBOP and DIPEA.

8. The method of claim 5, wherein the synthetic Pup of claim 1 or claim 4 is generated using Fmoc-based linear solid-phase peptide synthesis (SPPS) or intein-based chemistry.

9. A method for identifying a modulator of deamidase of Pup (Dop) activity, comprising:
   a) contacting the purified synthetic Pup of claim 1 or claim 4 with a test compound in the presence of deamidase of Pup (Dop), wherein the Dop cleaves the synthetic fluorogenic or luminescent reporter from the purified synthetic Pup of claim 1 or claim 4; and
   b) measuring the amount of cleaved synthetic fluorogenic or luminescent reporter in the presence and absence of the test compound, wherein the difference in amount of cleaved synthetic fluorogenic or luminescent reporter in presence of the test compound relative to that measured in the absence of the test compound identifies the test compound as a modulator of Dop activity.

10. The method of claim 9, wherein the fluorescent moiety is amino methyl coumarin (AMC) or 5-tetramethyl-rhodamine (TAMRA).

11. The method of claim 9, wherein the Dop is presented in a cell lysate.

12. The method of claim 11, wherein the cell lysate is isolated from a bacterial cell.

13. The method of claim 12, wherein the bacterial cell expresses endogenous Dop.

14. The method of claim 9, wherein the test compound is identified as an inhibitor of Dop activity.

* * * * *